US012629471B2

(12) United States Patent
Breton et al.

(10) Patent No.: US 12,629,471 B2
(45) Date of Patent: May 19, 2026

(54) METHOD AND SYSTEM OF CLOSED LOOP CONTROL IMPROVING GLYCEMIC RESPONSE FOLLOWING AN UNANNOUNCED SOURCE OF GLYCEMIC FLUCTUATION

(71) Applicant: University of Virginia Patent Foundation, Charlottesville, VA (US)

(72) Inventors: Marc D. Breton, Charlottesville, VA (US); Jose Garcia-Tirado, Charlottesville, VA (US); Jenny Diaz-Castaneda, Charlottesville, VA (US); Dayu Lv, Charlottesville, VA (US); John Corbett, San Diego, CA (US); Patricio Colmegna, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 583 days.

(21) Appl. No.: 18/031,976

(22) PCT Filed: Oct. 14, 2021

(86) PCT No.: PCT/US2021/054894
§ 371 (c)(1),
(2) Date: Apr. 14, 2023

(87) PCT Pub. No.: WO2022/081788
PCT Pub. Date: Apr. 21, 2022

(65) Prior Publication Data
US 2024/0024576 A1      Jan. 25, 2024

Related U.S. Application Data

(60) Provisional application No. 63/091,646, filed on Oct. 14, 2020.

(51) Int. Cl.
*A61M 5/172* (2006.01)
*A61B 5/00* (2006.01)
(Continued)

(52) U.S. Cl.
CPC .......... *A61M 5/1723* (2013.01); *G16H 20/17* (2018.01); *G16H 40/67* (2018.01); *G16H 50/20* (2018.01);
(Continued)

(58) Field of Classification Search
CPC .......... A61M 5/1723; A61M 2230/201; A61M 5/14244; A61M 2205/52;
(Continued)

(56) References Cited

U.S. PATENT DOCUMENTS

2008/0154513 A1    6/2008  Kovatchev et al.
2010/0292634 A1    11/2010  Kircher, Jr. et al.
(Continued)

FOREIGN PATENT DOCUMENTS

CN       104837517 A    8/2015
CN       108495665 A    9/2018
(Continued)

*Primary Examiner* — Jason E Flick
(74) *Attorney, Agent, or Firm* — Potomac Law Group, PLLC; Vincent M DeLuca; Brian H. Buck

(57) ABSTRACT
A method, system, and computer-readable medium are provided for a dual mode Closed-Loop Control (CLC) system integrating each of (i) an adaptive, personalized Model Predictive Control (MPC) control law that modulates the control strength of insulin infusion depending on recent past control actions, glucose measurements, and their derivative(s), (ii) an automatic Bolus Priming System (BPS) that commands additional insulin injections upon the detection of enabling metabolic conditions (e.g., an unannounced meal), and (iii) a hyperglycemia mitigation system (HMS) to avoid prevailing hyperglycemia.

20 Claims, 15 Drawing Sheets

(51) Int. Cl.

| | |
|---|---|
| *A61B 5/145* | (2006.01) |
| *G16H 20/17* | (2018.01) |
| *G16H 20/60* | (2018.01) |
| *G16H 40/67* | (2018.01) |
| *G16H 50/20* | (2018.01) |

(52) U.S. Cl.
CPC ....... *A61M 2230/201* (2013.01); *G16H 20/60* (2018.01)

(58) Field of Classification Search
CPC .. A61M 2230/005; A61M 2005/14208; A61M 2205/3553; A61M 2005/14296; A61M 5/14276; G16H 20/17; G16H 40/67; G16H 50/20; G16H 20/60; G16H 50/50; G16H 20/10; G16H 50/30; A61B 5/4839; A61B 5/7275; A61B 5/0022; A61B 5/14532; A61B 5/486; A61B 34/10
See application file for complete search history.

(56) References Cited

U.S. PATENT DOCUMENTS

| | | | |
|---|---|---|---|
| 2012/0078067 A1* | 3/2012 | Kovatchev ............. G16H 50/50 600/301 |
| 2014/0163517 A1* | 6/2014 | Finan ..................... G16H 50/20 604/504 |
| 2015/0018633 A1* | 1/2015 | Kovachev .............. A61B 5/746 600/301 |
| 2016/0193411 A1* | 7/2016 | Ljuhs .................. A61M 5/1723 702/19 |
| 2019/0336683 A1 | 11/2019 | O'Connor et al. |
| 2021/0282677 A1 | 9/2021 | Kovatchev et al. |

FOREIGN PATENT DOCUMENTS

| | | | | |
|---|---|---|---|---|
| CN | 108633250 A | 10/2018 | | |
| CN | 108697880 A | 10/2018 | | |
| JP | 2018528794 A | 10/2018 | | |
| JP | 2020511202 A | 4/2020 | | |
| WO | WO-2018009614 A1 * | 1/2018 | ........ | A61M 5/14244 |
| WO | 2019125932 A1 | 6/2019 | | |

* cited by examiner

METHOD AND SYSTEM OF CLOSED LOOP CONTROL IMPROVING GLYCEMIC RESPONSE FOLLOWING AN UNANNOUNCED SOURCE OF GLYCEMIC FLUCTUATION

CROSS-REFERENCE TO RELATED APPLICATION

This international application claims priority to and the benefit of U.S. Provisional Application No. 63/091,646 filed Oct. 14, 2020, the entire contents of which are incorporated by reference herein.

FIELD OF THE DISCLOSURE

Disclosed embodiments relate to providing improved glycemic control to individuals with Type 1 diabetes mellitus (T1DM; herein T1D), and more specifically, such improvement as may be implemented in accordance with Closed-Loop Control (CLC) so as to fully automate the rejection of glycemic disturbances owing to an absence of meal announcement.

BACKGROUND

T1D is a lifelong chronic metabolic disorder with a high economic, physical, social, and mental toll for both people with the condition and their caregivers.[1,2] This autoimmune condition results in absolute insulin deficiency and a life-long need of exogenous insulin to regulate blood glucose concentration.[3] Intensive Insulin Therapy (IIT) has shown to be effective in reducing average glycemia, which is typically assessed by hemoglobin A1c (HbA1c), further chronic complications, and possible comorbidities.[4,5] However, IIT is often associated with increased time in hypoglycemia (low blood glucose), which may be associated with serious complications and even death.[6] Conversely, systematic exposure to hyperglycemia (high blood glucose) has serious short and long-term implications on both health and life expectancy.[7] CLC, as may be implemented in an artificial pancreas (AP), ordinarily including an insulin infusion pump, continuous glucose monitor (CGM) and controlling algorithm therebetween, provides a convenient approach to automatically titrating insulin doses, which increases the amount of time spent in euglycemia (normal glucose levels) while significantly reducing the physical and mental burden typically associated with T1D.[8]

In the last decade, there has been a dramatic increase in both in-silico and in-vivo studies involving different types of APs.[9] This upswing may be attributed to advances in computer simulation, CGM, insulin pumps, and mobile platforms.[10] In this time, the field has seen a fast transition from the clinical bench[11] to the clinical practice of two (2) commercial hybrid APs in the U.S., and particularly the Medtronic Minimed 670G[12] and Tandem Control-IQ.[13,14] APs are characterized as "hybrid" when automatically modulating the insulin pump's infusions, yet are not designed to entirely replace carbohydrates coverage (i.e., the amount of insulin taken with a meal to counteract the glycemic effect of ingested carbohydrates). Given the mismatch between meal absorption and subcutaneous (s.c.) insulin time constants, mealtime insulin boluses must therefore be manually requested 10-15 minutes before the commencement of a meal and be proportional to an a priori meal-size estimation (often given by meal size or carbohydrate content). In contrast, fully automated APs expand the capabilities of hybrid APSs by automatically rejecting major disturbances in glycemic levels due to meals and physical activity.

In these regards, meals remain a hurdle for APs due to the large impact they have on glucose homeostasis.[15] Different carbohydrate amounts as well as the overall macronutrient composition of a meal may trigger diverse glucose dynamic responses even in optimal preprandial condition. Outstanding postprandial outcomes have been reported with hybrid APs when there is little or no uncertainty in the parameters (e.g., carbohydrate content, insulin-carbohydrate ratio (CR), and correction factor (CF)) which are used to compute the prandial insulin bolus.[13,16,17] However, relatively high uncertainty in these parameters seems to be the norm rather than the exception, which poses a risk to CLC performance and to overall glucose control.[18] Earlier contributions considering unannounced meal challenges with fully automated designs may be found in [19]-[24] from an engineering perspective (in-silico) and in [25]-[30] from a clinical perspective (in-vivo). In-silico studies reported on average percent time in range (TIR) [70-180] mg/dL spanning from 70.4 to 90.0% and percent time <70 mg/dL spanning from 0.0 to 4.04%, whereas, clinical studies reported the same metrics spanning from 63.6 to 84.7% and 0.1 to 2.9%, respectively.

However, while APs implementing CLC perform very well at managing glycemia in the absence of prandial glucose excursions (such as during the overnight period), it has been difficult to prevent prolonged hyperglycemia following consumption of carbohydrates that are not announced and for which a bolus is not administered.[55] This is partly because CLC systems experience inherent delays in CGM sensing of both rising prandial glucose levels and in the initiation of insulin action following its infusion, and also because CLC must also avoid hypoglycemia from over-aggressive insulin administration. Because of these considerations, all current commercially-available CLC system are actually hybrid closed-loop (HCL) systems that require the user to enter the quantity of carbohydrate ingested; receiving a prandial CR to avoid significant hyperglycemia.[56-60]

Unfortunately, it is common for individuals with T1D to omit bolusing for carbohydrates. This affects 65% of adolescents at least once weekly,[52] with 38% missing at least 15% of their boluses.[53] Adolescents who miss four boluses weekly experience an increase of 1% in their HbA1C,[52] which may contribute to the large number of adolescents who fail to meet recommendations for HbA1c levels.[54]

Thus, it would be desirable to provide for an optimization of CLC that automates bolusing, as appropriate, and does so in a manner that automatically modulates insulin delivery to reject, i.e., attenuate, glycemic disturbances tending toward hyperglycemia while inhibiting potential for hypoglycemia.

In these regards, results according to embodiments herein are compared with those obtained according to an established hybrid CLC controller, the USS-Virginia.[32]

In particular, such analyses and results are based on the 100 subjects adult cohort of the FDA-accepted UVA/Padova simulator relative to a variety of metabolic responses and population characteristics.[33]

SUMMARY

It is to be understood that both the following summary and the detailed description are exemplary and explanatory and are intended to provide further explanation of the present embodiments as claimed. Neither the summary nor the description that follows is intended to define or limit the scope of the present embodiments to the particular features mentioned in the summary or in the description. Rather, the scope of the present embodiments is defined by the appended claims.

An embodiment may include, in an artificial pancreas (AP), a processor-implemented method of regulating glycemia for a subject having Type 1 diabetes (T1D), including predicting glycemia values for the subject based on continuous glucose monitor (CGM) measurements of the subject; determining a schedule of basal insulin dosing according to the predicted values; modifying the schedule according to detection, from the CGM measurements, of a predetermined value of one or more of the CGM measurements and an increasing rate of change of the CGM measurements, and defining a modified schedule according to the modification; and delivering the schedule or the modified schedule to the subject. The embodiment may further include calculating a probability that a glycemic disturbance, which was not announced to the AP, occurred within a predetermined period; and supplementing the delivery of the schedule or the modified schedule with an automatic delivery of a first bolus of insulin in response to the calculated probability.

The schedule and the modified schedule may each minimize a cost function including terms to (a) correct the subject's glycemia level(s) to a predetermined target level, (b) penalize predicted glycemia values trending toward hypoglycemia, and (c) weight a difference amount between predictions of two consecutive basal insulin doses.

The glycemic disturbance may be defined by at least one source of glycemic fluctuation which is unaccounted for by the predicted glycemia values on which the schedule and the modified schedule are based, and the calculated probability may be based on the CGM measurements for the predetermined period.

The calculated probability may be calculated at each of successive intervals of the CGM measurements, each interval being included within the predetermined period.

The first bolus may be defined by predetermined percentage of total daily insulin (TDI) of the subject.

The predetermined percentage may increase as the calculated probability increases.

With respect to a series of first boluses, a subsequent one thereof may be decreased by an amount of insulin on board (JOB) equal to a sum of each of antecedent first boluses.

Based on the predicted glycemia values indicating hypoglycemia, as aspect may include automatically decreasing the basal insulin dosing to a fraction of an average therefor.

A further aspect may include automatically supplementing the delivery of the schedule or the modified schedule with a delivery of a second bolus of insulin (a) in response to a current estimated glycemia value and the predicted glycemia values indicating hyperglycemia and (b) after a predetermined time from the delivery of the first bolus.

The delivery of the second bolus may be blocked within two (2) hours after delivery of the first bolus.

A frequency of the delivery of the second bolus may be limited to once per hour.

A further aspect may include suspending the automatic delivery of the first bolus in response to announcement of a meal to the AP, and supplementing the delivery of the schedule or the modified schedule with a delivery of a third bolus calculated as up to one-half of a bolus based on the subject's insulin-carbohydrate ratio (CR) and a correction factor (CF).

Respective embodiments may further include a relative system and computer-readable medium commensurate with the embodied method above.

In certain embodiments, the disclosed embodiments may include one or more of the features described herein.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. Embodiments herein will be more particularly described in conjunction with the following drawings wherein.

DETAILED DESCRIPTION

Figure 1:
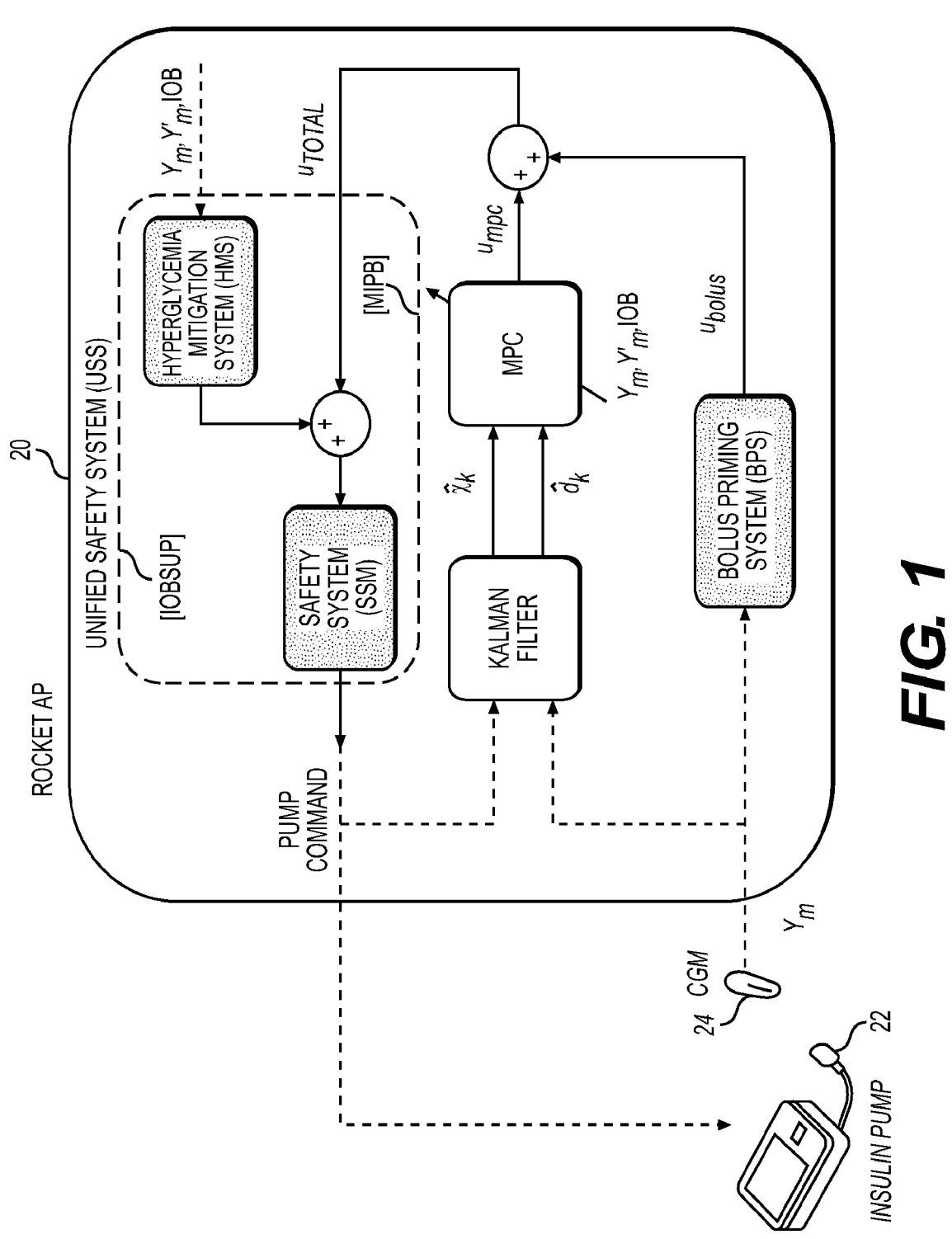
FIG. 1 illustrates a Closed-Loop Control (CLC) system implementing Model Predictive Control (MPC) according to embodiments herein.

The present disclosure will now be described in terms of various exemplary embodiments. This specification discloses one or more embodiments that incorporate features of the present embodiments. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. The skilled artisan will appreciate that a particular feature, structure, or characteristic described in connection with one embodiment is not necessarily limited to that embodiment but typically has relevance and applicability to one or more other embodiments.

In the several figures, like reference numerals may be used for like elements having like functions even in different drawings. The embodiments described, and their detailed construction and elements, are merely provided to assist in a comprehensive understanding of the present embodiments. Thus, it is apparent that the present embodiments may be carried out in a variety of ways, and does not require any of the specific features described herein. Also, well-known functions or constructions are not described in detail since they would obscure the present embodiments with unnecessary detail.

The description is not to be taken in a limiting sense, but is made merely for the purpose of illustrating the general principles of the present embodiments, since the scope of the present embodiments are best defined by the appended claims.

It should also be noted that in some alternative implementations, the blocks in a flowchart, the communications in a sequence-diagram, the states in a state-diagram, etc., may occur out of the orders illustrated in the figures. That is, the illustrated orders of the blocks/communications/states are not intended to be limiting. Rather, the illustrated blocks/communications/states may be reordered into any suitable order, and some of the blocks/communications/states could occur simultaneously.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. The word "exemplary" is used herein to mean "serving as an example, instance, or illustration." Any embodiment described herein as "exemplary" is not necessarily to be construed as preferred or advantageous over other embodiments. Additionally, all embodiments described herein should be considered exemplary unless otherwise stated.

It should be appreciated that any of the components or modules referred to with regards to any of the embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

Ranges may be expressed herein as from "about" or "approximately" one particular value and/or to "about" or "approximately" another particular value. When such a range is expressed, other exemplary embodiments include from the one particular value and/or to the other particular value.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

In accordance with the above-described goal and benefit of attaining and maintaining optimal TIR, we, the inventors at the University of Virginia (UVA) present a CLC system termed the Reactive Optimal Carbohydrates Kinetics EsTimation AP, or ROCKET AP (hereinafter "Rocket AP"). In doing so, it is contemplated that the Rocket AP may include Model Predictive Control (MPC) as implemented in a Diabetes Assistant (DiA) format 20 provided by, for example, a smartphone or other receiving and/or computing platform configured to enable communication among an insulin infusion pump 22 (e.g., Tandem t:slim X2™) and a Continuous Glucose Monitor (CGM) 24 (e.g., Dexcom G6™) (see FIG. 1) and the DiA. As such, the DiA may define a general control paradigm and may be referred to herein as a "controller" tasked with continually predicting future glycemia values and calculating optimal insulin doses to maintain an individual's target glucose level. Thus, in referring to FIG. 1, the controller may include and be defined by at least those components and functional flow as shown in the greyed portion thereof, and specifically one or more modules providing the MPC, a Kalman Filter, a Bolus Priming System (BPS), and Unified Safety System (USS) comprised of a Safety System Module (SSM) and Hyperglycemia Mitigation System (HMS). Additionally, the controller may include and implement as portions of the USS an Insulin-on-Board Supervisor (IOBSUP) and a Power Brakes (PB) module. Each aspect of the controller is discussed in detail in the discussion below. The controller may be configured to be either (a) fully automated so as to present full CLC (FCLC) by automatically rejecting the glycemic effect caused by carbohydrates of an unannounced meal and/or (b) operational as a hybrid CLC system by which a meal bolus may be provided in response to meal announcement. In FIG. 1, $y_m$, $y'_m$, and IOB represent the current CGM measurement, its time derivative and insulin on board, respectively. $\hat{x}_k$ and $\hat{d}_k$ represent the Kalman estimates of the glucose state and disturbance at time k, respectively, and $u_{bolus}$, $u_{mpc}$, and $u_{total}$ are discussed below.

In particular, the controller may be configured to predict glycemia values and calculate insulin dosages based on a variation of the model presented by Garcia-Tirado, et al.[34] that omits the oral submodel thereof and considers subcutaneous insulin transport infusion as a triangular submodel. Relative to the parameters and population values therefor as shown in Table 1 below, the predictive model implemented by the controller may be given as the following (according to its Equations 1-6):

$$\dot{G}(t) = -S_g G(t) + k_a - S_I X(t) G(t) + k_b d(t) \qquad (1)$$

$$\dot{X}(t) = -p_2 X(t) + p_2 I(t) \qquad (2)$$

$$\dot{I}_{sc1}(t) = -(k_1 + k_d) I_{sc1}(t) + u(t) \qquad (3)$$

$$\dot{I}_{sc2}(t) = -k_2 I_{sc2}(t) + k_d I_{sc1}(t) \qquad (4)$$

$$\dot{I}(t) = -nI(t) + k_c IR_a(t) \qquad (5)$$

with $$IR_a(t) = k_1 I_{sc1}(t) + k_2 I_{sc2}(t) \qquad (6)$$

where G (mg/dL) is the plasma glucose concentration, X (L/min) is the proportion of insulin in the remote compartment, $I_{sc1}$ (mU) and $I_{sc2}$ (mU) are the amounts of non-monomeric and monomeric insulin, respectively, in the subcutaneous space, I is the amount of plasma insulin (mU), d (mg/dL) is the disturbance input entering to the glucose dynamics, and u (mU/min) is the exogenous insulin input.

TABLE 1

| Symbol | Meaning | Value [Units] |
| --- | --- | --- |
| $S_z$ | Fractional glucose effectiveness | 0.01 [$min^{-1}$] |
| $k_a$ | Endogenous Glucose Production | 1.2 [mg/dL] |
| $k_b$ | rate constant | 0.0076 [$dL^{-1}$] |
| $k_c$ | rate constant | 0.1211 [$min^{-1}$] |
| $S_j$ | Insulin sensitivity | $1 \times 10^{-4}$ [$min^{-1}$ per mU/L] |
| $p_2$ | Rate constant | 0.02 [$min^{-1}$] |
| $k_1$ | Rate constant | 0.02 [$min^{-1}$] |
| $k_2$ | Rate constant | 0.02 [$min^{-1}$] |
| $k_d$ | Rate constant | 0.0164 [$min^{-1}$] |
| n | Rate constant | 0.178 [$min^{-1}$] |

Equations (1) to (5) are linearized at $(u_{op}, G_{op}) = (\bar{u}_b, 120)$, with $\bar{u}_b$ as the subject-specific basal insulin rate, and discretized with a sampling time $t_s = 5$ minutes to be embedded into the linear MPC framework $$x_{k+1} = Ax_k + B_I u_k + B_d d_k \qquad (7)$$

$$y_k = Cx_k \qquad (8)$$

where $x_k = [G_k, X_k, I_{sc1,k}, I_{sc2,k}, I_k] \in \mathbb{R}^5$ is the state vector, A, $B_I$, $B_d$, C are the matrices of the discrete-time linear system (Equations (7)-(8)) with corresponding dimensions, and $u_k$, $y_k \in \mathbb{R}$ are the insulin injection and glucose measurement deviations with respect to $u_{op}$ and $G_{op}$, respectively.

To estimate a current state and disturbance d, e.g., an unannounced meal, we assume that d is a disturbance that includes the unmodeled phenomena directly affecting glucose dynamics.[37] To that end, we augment Equation (7) with $d_{k+1} = d_k$, yielding $$\bar{x}_{k+1} = \bar{A}\bar{x}_k + \bar{B}_I u_k \qquad (9)$$

$$y_k = \bar{C}\bar{x}_k \qquad (10)$$

with $\bar{x}_k = [G_k, X_k, I_{sc1,k}, I_{sc2,k}, I_k, d_k]$ and $$\bar{A} = \begin{bmatrix} A & 0_{5 \times 1} \\ 0_{1 \times 5} & 1 \end{bmatrix}, \quad \bar{B}_I = \begin{bmatrix} B \\ 0 \end{bmatrix}, \quad \bar{C} = [C \quad 0]$$

Modeling the disturbance as a constant dynamic allows the state estimator, embodied by the Kalman filter of FIG. 1, to correct the disturbance entering the main dynamics.

In order to conform the model to a specific subject and to contextualize quantites shown in FIG. 1 and including $y_m$, $y'_m$, (i.e., current CGM measurement and its time derivative), IOB, $\hat{x}_k$ and $\hat{d}_k$ (i.e., Kalman estimates of the state and disturbance at time k), the model in Equation (9) is individualized upon consideration of $\theta_{ide} = [S_g k_b k_a S_I p_2]$ as the parameter set to be found using CGM and insulin records from a 14-day data collection period. The remaining parameters are set to population values since they are deemed not identifiable. Model individualization is carried out in a three-step procedure, in which (i) data is cleaned for data gaps and compression artifacts, (ii) the disturbance signature d is estimated for the entire data collection period using the Kalman filter and Equation (9) with population values, and (iii) the model is identified and validated after splitting the available data into identification and validation data sets using the estimated disturbance in (ii). The prediction ability for each model is assessed using the Root Mean Square Error (RMSE) metric $$RMSE = \frac{1}{\sqrt{N}} \|\tilde{y} - \tilde{y}_m\| \qquad (11)$$

where N is the number of data points, $\tilde{y}_m$ is the CGM data, and $\tilde{y}$ is the output prediction using the identified model. Equation (9) does not explicitly consider meals as inputs. Instead, in the FCLC mode of the controller presented herein, d will inform the controller as soon as a meal begins to affect CGM values.

1) MPC

Based on the individualization and any detected disturbance d, MPC may command the controller to deliver basal insulin dosing (i.e., microboluses) every five (5) minutes, and to do so by modulating the aggressiveness or amount of such dosing as a function of the rate of glucose change. In this way, the MPC is optimized, as discussed below, relative to a predetermined, fixed target glucose level, e.g., 120 mg/dL, such that hypoglycemic and hyperglycemic events may be substantially avoided. The MPC may be embodied according to the following:[39,40]

$$\min_{\tilde{u}, \tilde{\eta}} \Phi^{mpc} \qquad (12a)$$

$$\text{s.t. model } (9) - (9)(10) \qquad (12b)$$

$$u_{min} \le u_j \le u_{max} \qquad (12c)$$

$$\Delta u_{min} \le \Delta u_j \le \Delta u_{max} \qquad (12d)$$

$$y_{min} - y_j \le \eta_j \qquad (12e)$$

$$\eta_j \ge 0 \qquad (12f)$$

with 12b, 12e, and 12f as $\forall j \in [1 \ldots, N_p]$ and 12c and 12d as $\forall j \in [1, \ldots, N_c-1]$, and $N_p$ and $N_c$ as the prediction and control horizons, respectively. $\tilde{u} = [u_1 \, u_2 \ldots u_{N_c-1}]$ represents the control policy and $\tilde{\eta}=[\eta_1\ \eta_2\ \ldots\ \eta_{N_p-1}]$ a policy of slack variables. $\tilde{\eta}$ is implements a softening of the hypoglycemia constraint $y_j \geq y_{min} \forall j \in \{1, \ldots, N_p\}$ yielding Equations (12e)-(12f). Equations (12c) and (12d) ensure that the control input and the difference $\Delta u_j = u_j - u_{j-1}$ lie into the intervals $[u_{min}, u_{max}]$ and $[\Delta u_{min}, \Delta u_{max}] \forall j \in \{0, \ldots, N_c-1\}$, respectively. The cost $\Phi^{mpc}$ in (12a) varies as a function of the IOB and the insulin rate of change. IOB is a widely used construct in APS that prevents the closed-loop system from stacking insulin as a consequence of the delay in the insulin action.[41] Every time an amount of insulin is injected, it sums up into a decay curve accounting for the circulating insulin.

The cost function in (12a) may be defined as $$\Phi^{mpc} = \Sigma_{j=1}^{N_p} Q_z(IOB)\bar{y}_j^2 + \kappa\eta_j^2 + \Sigma_{j=1}^{N_c-1}\lambda_1(y_m, y_{m'})\Delta u_j^2 \qquad (13)$$

with $\bar{y}_j = y_j - r_j$ as the glucose target error at the j-th step; $r_k$ as defined below is an asymmetric time-varying exponential reference signal,[31,34,42,43] and $\kappa$ as a constant penalizing predictions trending towards hypoglycemia. $Q_z(IOB)$ weights the difference between model prediction $\tilde{y}$ and the evolution of the controller's reference $\tilde{r}$ as a function of the JOB, and is given by $$Q_z(IOB) = \begin{cases} Q_0 & \text{if } IOB < IOB_{min} \\ m \cdot IOB + Q_0 & \text{if } IOB \in [IOB_{min}, TDI/\alpha] \\ Q_0/\beta & \text{if } IOB > TDI/\alpha \end{cases} \qquad (14)$$

with $Q_0=10$ as the nominal weight for $Q_z(IOB)$, TDI as the user-specific total daily insulin, $IOB_{min}=TDI/40$, and $\alpha=30$ and $\beta=1000$ as tunable parameters. The slope of the detuning rule is defined as $$m = \frac{Q_0 \cdot \alpha \cdot (1-\beta)}{\beta \cdot (TDI - \alpha \cdot IOB_{min})}.$$

As such, a respective microbolus may be determined in accordance with the minimization of the cost function to include $\bar{y}_j$ as a term correcting an individual's glucose concentration to a target value; $\bar{\kappa}$ as a term penalizing low glucose values; and $Q_z(IOB)$ as a regularization term weighting the difference between two (2) consecutive microboluses. Such minimization may be achieved in accordance, i.e., to satisfy, a predetermined dosage window of, optionally, two (2) hours, and thus define a schedule of basal insulin infusion ($u_{mpc}$ in FIG. 1) for a given subject. That is, the MPC may request deviation from a fixed basal rate so as to yield optimal dosing for that window. The minimization calculation may be performed successively for each of five (5) minute intervals and performed for the instant one thereof prior to a next iteration.

Figure 2A:
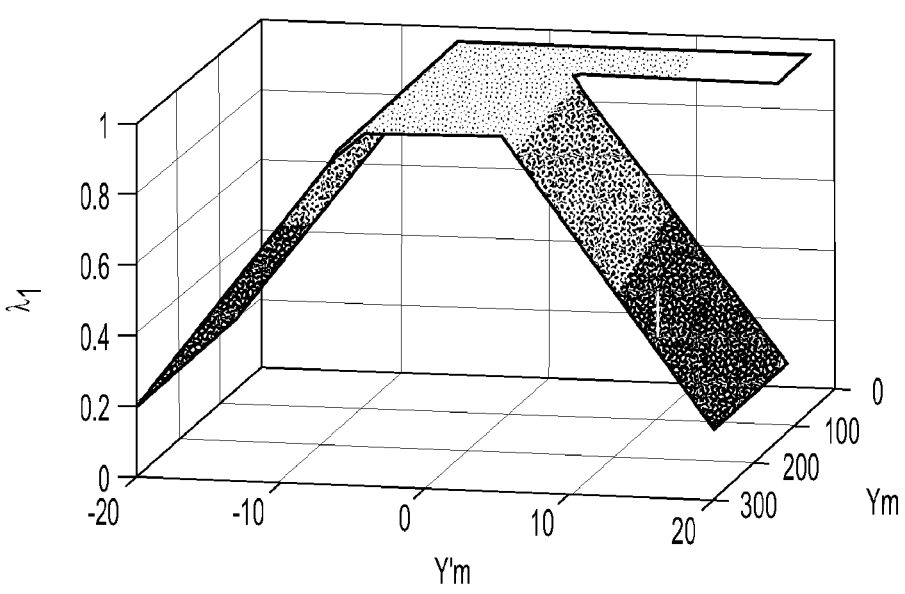
FIG. 2A illustrates a tuning/detuning surface according to the MPC of FIG. 1.
Figure 2B:
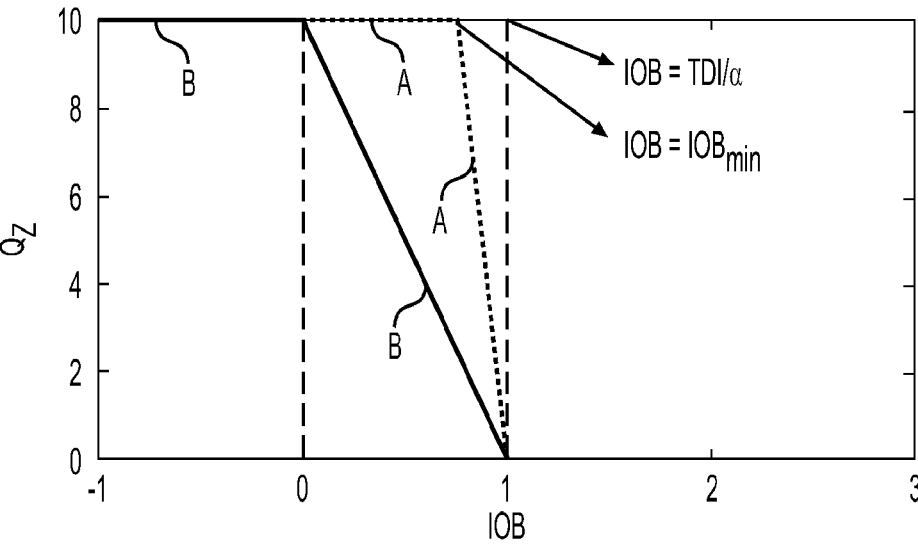
FIG. 2B illustrates a tuning/detuning rule according to the MPC of FIG. 1 and the tuning/detuning surface of FIG. 2A, according to embodiments herein.

Optimization of the tuning/detuning strategy for allows for more aggressive controller reactions at both high rate of CGM change and high blood glucose (BG) levels as depicted in Equation (15) below, where $y_m$ and $y'_m$ represent the current CGM value and the first derivative of the CGM trace at the current sampling time, respectively, $\lambda_{1,nom}=5/u_b$ represents the nominal value of $\lambda_1$, $st^+=5$ and $st^-=-5$ represent positive and negative slope thresholds, respectively, and $m_1=-0.8$ and $m_2=0.8$ represent the tuning/detuning slopes. In this way, $\lambda_1$ represents an inertial degree of deviation (from scheduled basal infusion) in response to a rate of change in CGM levels and high BG levels. In referring to FIG. 2, there is provided a graphical overview of the design of $\lambda_1$ and tuning/detuning $Q_z(IOB)$ at "A" (and relative to that of a predecessor format[31] at "B"), wherein $st^+$, and $m_{1,2}$ were found heuristically based on physiologic knowledge, and $\alpha$, $IOB_{min}$, and $\lambda_{1,nom}$ were found through grid search to obtain the best controller performance in terms of percentages of TIR, time <70 mg/dL, and time >180 mg/dL for all of the adult cohort of the UVA/Padova simulator.[44] Defining $IOB_{min}$, as above, allows for more aggressive controller action over an extended period of time immediately following commencement of a disturbance d, such that this increased controller action may yield a modified schedule of basal insulin infusion (i.e., a modification of $u_{mpc}$ in FIG. 1) for a subject.

$$\lambda_1(y_m, y_{m'}) = \begin{cases} \lambda_{1,nom} & \text{if } y_m > 40 \wedge y_{m'} \geq st^- \\ f_1(y'_m) & \text{if } y_m \geq 120 \wedge y_{m'} \geq st^+ \\ f_2(y'_m) & \text{if } y_m \geq 40 \wedge y_{m'} \leq st^- \end{cases} \qquad (15)$$

$$\text{s.t.} 0.2 \cdot \lambda_{1,nom} \leq \lambda_1(y_m, y_{m'}) \leq \lambda_{1,nom}, \text{ with}$$

$$f_1(y'_m) = m_1 \cdot \lambda_{1,nom} \cdot (y_{m'} - st^-) + \lambda_{1,nom}$$

$$f_2(y'_m) = m_2 \cdot \lambda_{1,nom} \cdot (y_{m'} - st^+) + \lambda_{1,nom}$$

Finally, the reference trajectory is defined as in Garcia-Tirado, et al.[31], in which $$r_j = \begin{cases} (y - y_{sp}) \cdot e^{-j/\tau^+} & \text{if } y \geq y_{sp} \\ 0 & \text{if } y < y_{sp} \end{cases} \qquad (16)$$

$\forall j \in \{0, \ldots, N_p-1\}$, and $y_{sp}$ represents the target or set point and $\tau_r^+$ represents a time constant used to modulate how the controller approaches the set point. The remaining parameter values of the controller are summarized in Table 2 below.

TABLE 2

| Parameter | Valve | Parameter | Value |
|---|---|---|---|
| $N_p$ | 24 | $N_p$ | 18 |
| $u_{min}$ | $-u_b$ [mU/min] | $u_{max}$ | 100 [mU/min] |
| $\kappa$ | 100 | $\Delta u_{max}$ | 50 [mU/min] |
| $r_y^+$ | 10 [min] | $y_{min}$ | 70 [mg/dL] |
| $\lambda_{1,nom}$ | $5/u_b$ | TDI | user-specific [U] |

2) BPS

As has been discussed above, disruptions in efforts to maintain euglycemia that are brought about by the carbohydrate amount and composition of unannounced meals present a significant challenge to diabetes care and treatment. This is particularly the case since conventional CLC systems experience inherent delays in CGM sensing of rising prandial glucose levels and in the initiation of insulin action following infusion. Accordingly, we have recognized a need to counter the effect of such unannounced meals before such CLC systems may provide corrective action through microbolusing according to the aforementioned schedule or modified schedule for basal infusion. In the absence of providing such countering measures, individuals with T1D are prone to experience significant levels of hyperglycemia.

Accordingly, we present herein the Bolus Priming System, or BPS, as a module configured to cooperate alongside the above-discussed MPC to cause the punctual and automatic infusion of comparatively large amounts of insulin computed as fractions of total daily insulin (TDI). More specifically, such fractions may progressively increase in accordance with a calculated estimation of a probability that a large glycemic disturbance has occurred and which comprises and/or describes at least one source of glycemic fluctuation which is unaccounted for by the predicted glycemia values on which the schedule and the modified schedule are based. Such a source may comprise an unannounced meal having a significant carbohydrate composition (see discussion below with respect to amount of carbohydrate). In these regards, the term "unaccounted for" may mean substantially not fully explained, only partially explained, or not explained. This way, an infusion defining a first bolus herein ($u_{bolus}$ in FIG. 1) and which is caused by the BPS may immediately address what would otherwise result in a hyperglycemic event.

In particular, the BPS may be configured to operate at each of five (5) minutes intervals to examine whether, i.e., retrospectively, the probability that a meal-like disturbance d has occurred within the prior 30 minutes. To do so, a $2^{nd}$ order polynomial is fitted onto the last 30 minutes of CGM data generating the equation:

$$y_p(i) = p_1 i^2 + p_2 i + p_3$$

where $y_p(i)$ represents the glucose value at i=1, . . . , 6, representing the sequence of past 30 minutes of CGM data. The coefficients of this equation, $p_1$, $p_2$, $p_3$, may be used as features in a logistic regression classification algorithm. The output, $y_{log}$, may be defined as $$y_{log} = \beta_0 + \beta_1 \frac{p_1 - \sigma_{p_1}}{\mu_{p_1}} + \beta_2 \frac{p_2 - \sigma_{p_2}}{\mu_{p_2}} + \beta_3 \frac{p_3 - \sigma_{p_3}}{\mu_{p_3}}$$

where $\beta_0$, $\beta_1$, $\beta_2$, and $\beta_3$ were found using a simulation dataset where postprandial periods of time were labeled and the algorithm was trained for detection. For this equation, we normalized the features with their respective standard deviation, $\sigma_{1,2,3}$, and mean, $\mu_{1,2,3}$, as found from data collected from real subjects, under usual care, throughout a pre-admission data collection period.[45] The values of each of the coefficients and normalizing parameters are listed in Table 3 below (with parameter values in mg/dL). The disturbance probability at each iteration, $\pi_k$ may be found using the following equation, in which $$\pi_k = \frac{1}{1 + e^{-y_{log}}}.$$

TABLE 3

| Symbol | Value |
| --- | --- |
| $\beta_0$ | −2.1080 |
| $\beta_1$ | 1.7289 |
| $\beta_2$ | 1.5894 |

TABLE 3-continued

| Symbol | Value |
| --- | --- |
| $\beta_3$ | 0.0688 |
| $\sigma_{p1}$ | 3.4991 |
| $\sigma_{p2}$ | 9.5220 |
| $\sigma_{p3}$ | 58.3417 |
| $\mu_{p1}$ | $3.0 \times 10^{-4}$ |
| $\mu_{p2}$ | −0.0122 |
| $\mu_{p3}$ | $1.5 * 10^{-2}$ |

This probability may then be used to determine if a bolus is required, and if so, how much insulin should be delivered. The BPS contemplates a predetermined schedule describing what percent of an individual's TDI amount $P_{TDI}$ should be administered at each probability threshold. That schedule is provided below, and exhibits probability determinations increasing from 0.3 to 0.9.

$$P_{TDI} = \begin{cases} 3\% & \text{if } 0.3 \le \pi_k < 0.5 \\ 5\% & \text{if } 0.5 \le \pi_k < 0.7 \\ 6\% & \text{if } 0.7 \le \pi_k < 0.9 \\ 7\% & \text{if } \pi_k \ge 0.9 \end{cases} \tag{17}$$

Before a BPS bolus is delivered, the amount of IOB from antecedent BPS doses is subtracted. This bolus is computed as $$J_{BPS} = \max\left(P_{TDI} \cdot TDI - \frac{IOB_{BPS}}{TDI}, 0\right)$$

where $J_{BPS}$ represents the amount of insulin delivered by the BPS, $P_{TCI}(\%)$ is the percentage of the patient's TDI requested based on the dosing schedule above and $IOB_{BPS}$ is the amount of insulin on board from previous meal-related BPS doses. $IOB_{BPS}$ may be found using a 6-hour IOB curve.[46] The $J_{BPS}$ doses may be saturated at 0 to prevent the system from commanding negative insulin doses. In these ways, the BPS delivers at least two (2) safeguards tending to avoid hypoglycemia. First, the $J_{BPS}$ dose is adjusted based on previously injected priming doses. Second, a threshold, BPS_threshold is set to allow priming doses only when glucose concentration is greater than such threshold. The BPS_threshold may be determined by the following:

$$\text{t\_prev\_hypo} := \text{minute of last } BG \le 70 \text{ mg/dL}$$

$$\text{BPS\_threshold} = \begin{cases} 160 - \frac{4}{3} * \text{t\_prev\_hypo} & 0 \le \text{t\_prev\_hypo} \le 60 \\ 80 & \text{t\_prev\_hypo} > 60 \end{cases}$$

The disturbance probability thresholds together with their corresponding insulin doses were determined through the use of a method that has been employed before to "replay" past real data using regularized deconvolution to solve for unknown inputs into the glucose-insulin model.[36,47] The method determines sources of glycemic variability not described through the insulin and meal record, allowing the alteration of insulin doses and simulation of a resultant effect on blood glucose values (simulation replay). Using data from the collection period from a past study (ClinicalTrials.gov NCT03859401), we were able to determine an initial numerical correspondence among different probability thresholds [0.1-1.0] and different insulin boluses, as percentages of the TDI [3%-9%].

After each automatic bolus (computed based on prevailing CGM values at each epoch of the collected data), we used the technique described above to simulate the next two (2) hours of glucose values and determined if this bolus could have caused a hypoglycemic event (CGM<70 mg/dL). We empirically set the maximum number of hypoglycemia events at one event per day.

Figure 3:
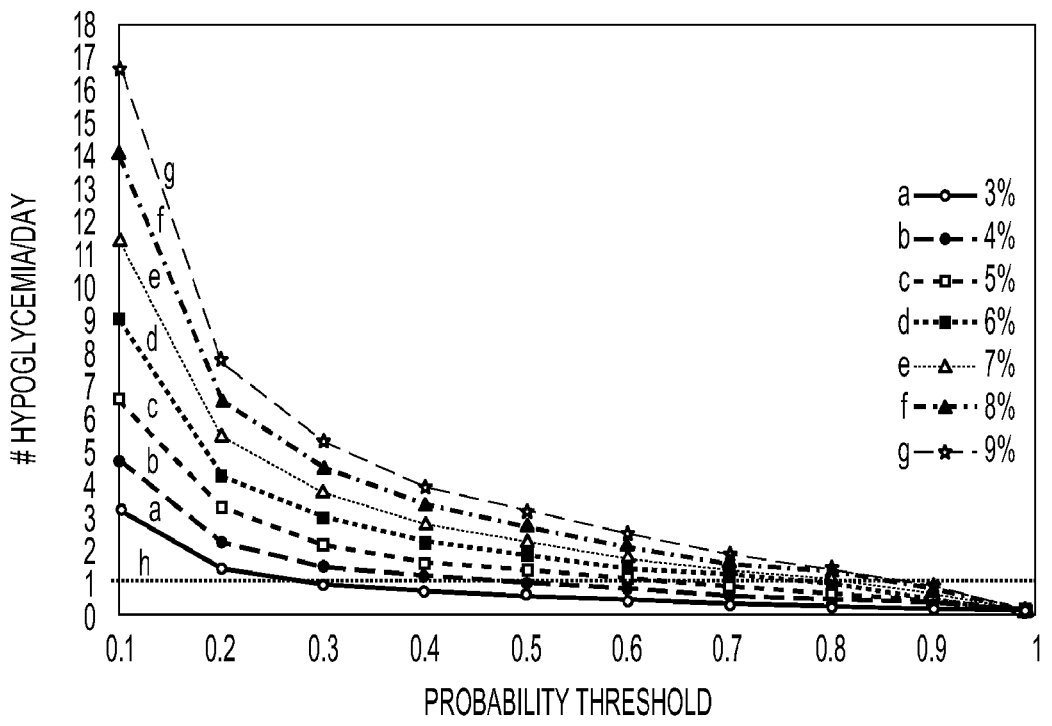
FIG. 3 illustrates a relative comparison of an amount of hypoglycemic events induced by Total Daily Insulin (TDI) as against a probability of glycemic disturbance.

FIG. 3 shows the results of the replay experiment where the BPS was evaluated. It may be clearly seen that low probability thresholds and high TDI amounts produced the most additional hypoglycemia. As probability thresholds increased and TDI percentages decreased, there was less observed hypoglycemia. The results of this study led us to determine that at probability thresholds of 0.3, 0.5, 0.7, 0.8, and 0.9, 3%, 4%, 5%, 6%, and 9% of TDI should be delivered, respectively.

Thus, as may be understood from the above, the controller according to FIG. 1 may be configured to operate in a first, or FCLC, mode such that glycemic disturbances resulting from unannounced meal/carbohydrate ingestion may be automatically rejected, i.e., without user intervention. As will be further understood, fulfillment of that rejection may be based on a retrospective examination of past CGM data yielding a determination of probable meal intake that supplants alternative meal announcement.

Additionally, though the controller according to FIG. 1 may be configured to operate in the first mode, as mentioned, operation in a second, or hybrid CLC (HCLC), mode is also contemplated such that standard meal announcement and controller actuated bolusing is implemented. In such a case, meals are announced and a meal bolus, referred to herein as a third bolus, is computed as up to 50%, i.e., 1%-50%, of the bolus calculated from the subject's CR and CF. In this case, the controller recognizes the announcement, thus suspending any impending or simultaneous BPS bolus.

3) USS (SSM and HMS)

With continued reference to FIG. 1, the USS thereof includes both the Safety System Module (SSM) and Hyperglycemia Mitigation System (HMS) module to counter potential for hypoglycemic and hyperglycemic events, respectively.

Specifically, the SSM evaluates $u_{total}$ (FIG. 1) and supervises the hypoglycemic-related risk linked to the controller's basal modulation by means of a short term (30 minutes) glycemic prediction and a risk space transform.[48] This module automatically saturates the insulin command to a fraction of the user average basal rate if hypoglycemia risk is predicted, and otherwise allows the command to pass through.

In this regard, the SSM may implement an Insulin on Board Supervisor (IOBSUP) module that serves to estimate IOB at each of five (5) minute successive intervals. With this estimate, the IOBSUP then broadcasts the estimate to all other modules to mitigate any risk of insulin stacking. Relative to the computation below, IOB is computed based on a four (4) hour action curve derived from Swan et al., (Diabetes Care 2009), i.e., insulin is considered as being depleted from an individual's system four (4) hours after injection.

J (as a vector of past insulin injection in 5 minute increments) is corrected for the basal insulin infusion (basal_hist):

$$J\_diff_k = J_k - \frac{basal\_hist_k}{12},$$

IOB is then computed as IOB=J_diff×Action_curve.

The SSM may also command to the controller to operate in a HYPOSAFE mode to deter significant hypoglycemic events by constraining insulin injections to be less than or equal to basal levels for one (1) hour after hypoglycemia is detected and announced. The logic underlying this mode is expressed below, such that Consider diff_rate as the differential basal rate (with sign) added to basal levels as the result of the controller decision making.

```
READ last_hypo_time from database
IF current_time - last_hypo_time ≤ 60 min
    IF diff_rate ≥ 0
        injection_sent_to_pump = u_basal
    ELSE
        injection_sent_to_pump = u_basal + diff_rate
    END
END
``` where in the else condition, diff_rate is adapted with a minus sign tending to keep insulin levels below basal values.

The SSM may further implement a Meal Informed Power Brakes (MIPB) module which is active at all times to veto any insulin delivery request by any other module. In particular, the MIPB module computes every 5 minutes an estimate of the patient metabolic status using the Kalman filter discussed above; it uses the metabolic state (a combination of the feedforward model states and the Kalman filter estimated states) to make a 10 minute, 30 minute and 60 minute glycemic prediction based on two different assumptions: (i) no insulin injected for the 10 minute prediction, and (ii) basal rate injected for the 30 and 60 minute predictions. The 10 minute and 60 minute predictions are broadcasted to the other modules, while the 30 minute predictions are used to compute the predicted glycemic risk. Based on that predicted risk, the MIPB then dampens the basal rate to generate an insulin constraint which is then compared to any received injection request, and the minimum of the constraint or the requests is then sent to the pump for injection. The braking action may be understood relative to the following set of parameters and implementation thereof at the controller.

| Name | Description | Units |
|---|---|---|
| $\hat{x}^+$ | Estimated state | N.A |
| $\hat{x}_{cl}^+$ | Closed-loop estimate | N.A |
| $G_{est}$ | Estimated glucose (current time) | mg/dl |
| $G_{sp}$ | Basal glucose concentration | mg/dl |
| $G_{pred, 30}$ | 30-min glucose prediction | mg/dl |
| $G_{pred, light}$ | Plasma glucose 10 min prediction with no insulin assumption for the red light | mg/dl |
| BrakeAction | Reduction amount imposed by the power brakes | N.A |

US 12,629,471 B2

17
-continued

| Name | Description | Units |
|---|---|---|
| Kbrakes | Braking coefficient | none |
| Const | Safety System constraint | $U \cdot hr^{-1}$ |
| $U_{sugg}$ | Final insulin dose | U |
| basal | basal rate value at execution time | U/hr |
| dU | output of Rocket AP | U |
| $u_b$ | basal rate value at execution time | mU/min |

Create the vector of estimated states:

$$\hat{x}^+ = [\, G \quad X_{cl} \quad d \quad X_{ol} \quad I_{sc1} \quad I_{sc2} \quad I \,]$$

18
Create the output variable $G_{est}$:

$$G_{est} = \hat{G}_{cl}^+(k) + G_{sp}$$

where $G_{sp}$ is the basal glucose concentration.

Using TMM—$\Delta X$ and the new state vector (for prediction)

$$\hat{x}_p^+ = [\, G \quad \Delta X \quad X_{ol} \quad d \quad I_{sc1} \quad I_{sc2} \quad I_p \,]$$

we compute $G_{pred,30}$ and $G_{pred,light}$:

$$G_{pred,30} = A_p^6 \cdot \hat{x}^+ + G_{sp}$$

$$G_{pred,light} = A_p^2 \cdot \hat{x}^+ + \Xi_2 \cdot u_b + G_{sp}, \text{ with } \Xi_2 = A_p B_{I,p} + B_{i,p}.$$

where $\Delta X = X_{cl} - X_{ol}$ and $A_p$ and $B_{I,p}$ are the state and input (insulin) matrices of the linearized TMM–$\Delta X$.

Compute the Brake Action $$Risk_k = \begin{cases} 10*(1.509*(\exp(1.084*\log(\log(Gpred_k))) - 5.381))^2 & if \ Gpred_k \le 112.5 \\ 0 \ \text{otherwise} \end{cases}$$

$$RiskEX_k = \begin{cases} 10*(0.9283*(\exp(1.8115*\log(\log(Gpred_k))) - 18.0696))^2 & if \ Gpred_k \le 140 \\ 0 \ \text{otherwise} \end{cases}$$

$$BrakeAction = \frac{1}{1 + Kbrakes*(EX*RiskEX_k + (1 - EX)*Risk_k)}$$

And finally compute the Safety System Constraint:

$$Cons = BrakeAction \cdot u_i$$

The final dose is the computed as follows:

> IF (BrakeAction < 1)
> $$U_{sugg} = \min\left(Const, \frac{basal}{12} + dU\right)$$
> ELSE
> $$U_{sugg} = \frac{basal}{12} + dU$$
> END As such, the SSM may accept or veto all or a portion of an requested injection amount. Additionally, the SSM, through an interface of the DiA, may request manual confirmation of a requested injection amount from a user of the controller. Through the interface, outputs from the MIPB and IOBSUP are combined to determine a Hypoglycemia and Hyperglycemia Red Light System, informing the patient of the hypoglycemic risk status (i.e., green, no perceived risk; yellow, predicted risk resulting in insulin dampening; and red, predicted imminent hypoglycemia with an external intervention needed); and hyperglycemic risk status (i.e., green, no perceived risk; yellow, predicted risk resulting in basal rate increase; and red, perceived hyperglycemia with an external intervention needed).

The HMS module, on the other hand, monitors BG level estimates and automatically commands one or more insulin correction boluses, referred to herein as second boluses, to counteract prevailing hyperglycemia. A command frequency is saturated to allow commands to occur, at most, once per hour, and any correction bolus to be issued by the HMS is blocked within a predetermined time, and optionally two (2) hours, from a first, i.e., BPS, bolus. That is, a HMS bolus may not be issued within a two (2) window after issuance of BPS bolus. A correction is considered every five (5) minutes, and issued if $G_k > 180$ mg/dL (current estimated glucose) and the CGM trend (computed as the slope coefficient of a CGM sum of square regression) is either flat or increasing (defined as $> -1$ mg/dL·min). The HMS-related correction bolus may be computed to correct the glucose level to, optionally, 110 mg/dL, according to Equation (18) below, in which $$HMS_{corr} = HMS_{ratio} \cdot HMS_{ini} \qquad (18)$$

with $$HMS_{ratio} = \begin{cases} 1 & y_{m'} \geq 1 \\ 0.5 \cdot y'_m + 0.5 & -1 \leq y'_m \leq 1 \\ 0 & y'_m \leq -1 \end{cases} \qquad (19)$$

$$HMS_{ini} = \frac{y_k^{abs} - G_{op}}{CF} - IOB \qquad (20)$$

with $$y_m^{abs}$$

as the current absolute CGM value. $HMS_{ratio}$ is a term attenuating the initial computed correction $HMS_{ini}$.

In Silico Study

Results were obtained using the entire adult cohort of 100 virtual subjects in the FDA accepted UVA/Padova simulator, with demographics summarized in Table 4 below.[33] Dawn phenomena and both intrapersonal and interpersonal insulin sensitivity variations were included in the experimental setup. The controller of FIG. 1 was challenged with a complete battery of experiments including not only the upcoming clinical scenario (discussed below), but also robustness tests with respect to variation in meal size. Specifically, the following results, including (A) model individualization, (B) performance of the BPS, and (C) overall controller performance to the nominal clinical scenario including announced and unannounced meals and a variation in the carbohydrate content for an unannounced dinner. The USS Virginia was used as the baseline controller.[32]

TABLE 4

| Parameter | Units | Mean ± SD | Min | Max |
|---|---|---|---|---|
| Body weight | kg | 75.2 ± 12.1 | 52.6 | 108.4 |
| TDI | IU | 42.8 ± 18.6 | 21.7 | 109.9 |
| Fasting BG | mg/dL | 119.1 ± 7.1 | 102.1 | 134.5 |

A) Model Individualization

To obtain a subject-specific controller design, subjects underwent a 14-day data collection period prior-to-admission. Data collection included various meals during the day with varying meal sizes and times. Daily data sets were split randomly into either identification (5 days) or validation (9 days).

Figures 4A, 4B:
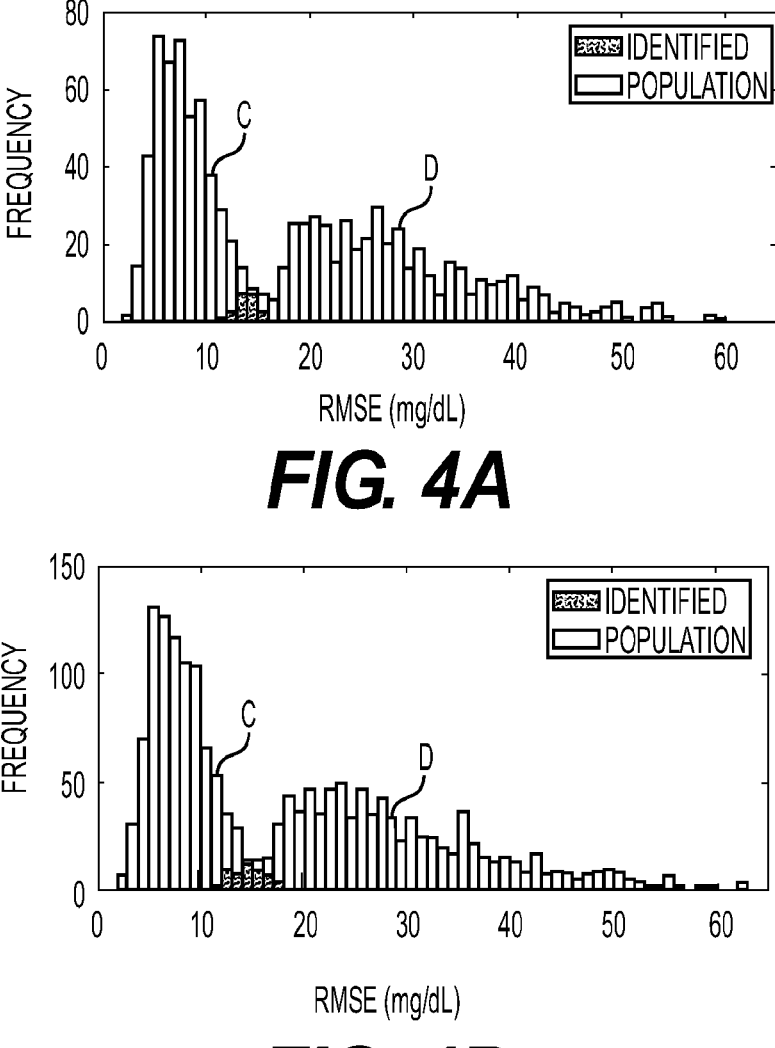
FIGS. 4A and 4B illustrate, relative to conducted in silico study of the CLC herein, histograms of Root Mean Square Error (RMSE) as to identification and validation data sets, respectively, across study subjects.

FIGS. 4A and 4B show the histograms for the daily identification and validation RMSEs, respectively, contrasting the identified models vs the model with population values for all virtual subjects in the adult cohort. Table 5 below shows additional statistics which assisted assessing the benefit of model individualization.

TABLE 5

| Statistic | Identified | Population |
|---|---|---|
| Identification | | |
| min RMSE [mg/dL] | 2.85 | 12.0 |
| max RMSE [mg/dL] | 17.02 | 59.23 |
| median RMSE [mg/dL] | 7.67 | 26.67 |
| Validation | | |
| min RMSE [mg/dL] | 2.79 | 11.88 |
| max RMSE [mg/dL] | 18.5 | 62.86 |
| median RMSE [mg/dL] | 7.73 | 26.56 |

B) BPS Performance

Figure 5:
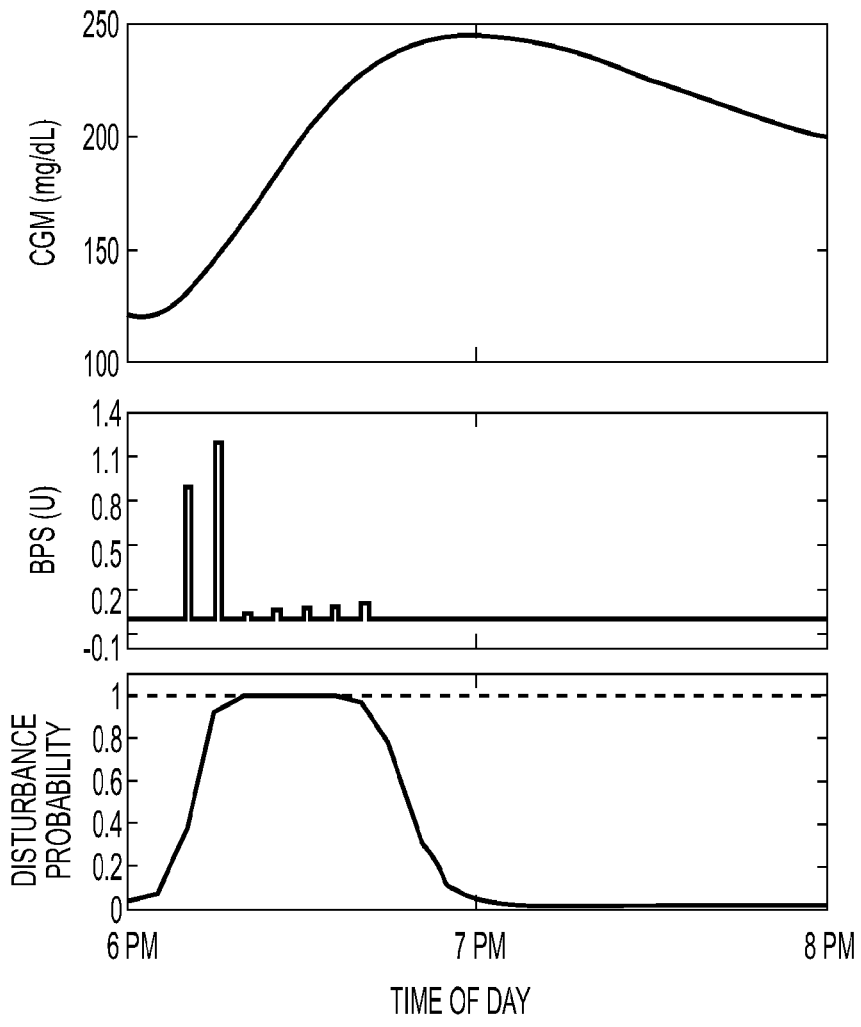
FIG. 5 illustrates an instance of performance of a Bolus Priming System (BPS) as provided by the MPC herein for a representative subject of the conducted in silico study.
Figure 6:
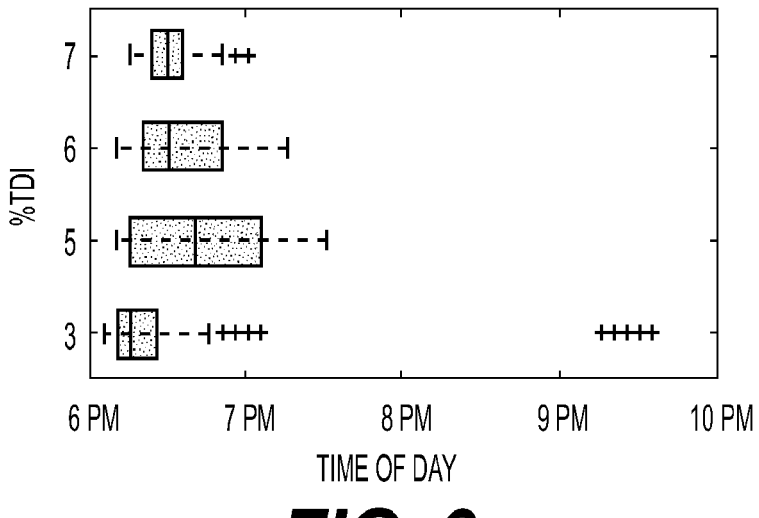
FIG. 6 illustrates a timing distribution of sequential injections for an unannounced meal for the entire cohort of the in silico study.

FIG. 5 illustrates the performance of the BPS for a representative subject in the simulator. The controller of FIG. 1 automatically commanded multiple safe boluses (total 2.47 U vs. 6.33 U as to USS Virginia) after an 80 g carbohydrate meal was given at 6 p.m. In total, the controller caused the infusion of 2.47 U in a cased of an unannounced meal versus an infusion of 3.16 U and 6.33 U (as to USS Virginia) that would have otherwise occurred in a case of an announced meal. In particular, it may be seen in FIG. 5 that the Rocket AP controller accurately predicted the disturbance owing to the 6 p.m. meal relative to to the shown CGM values. FIG. 6 shows the timing distribution of the sequential injections for the unannounced 80 g carbohydrate meal for the entire adult cohort.

Figure 7:
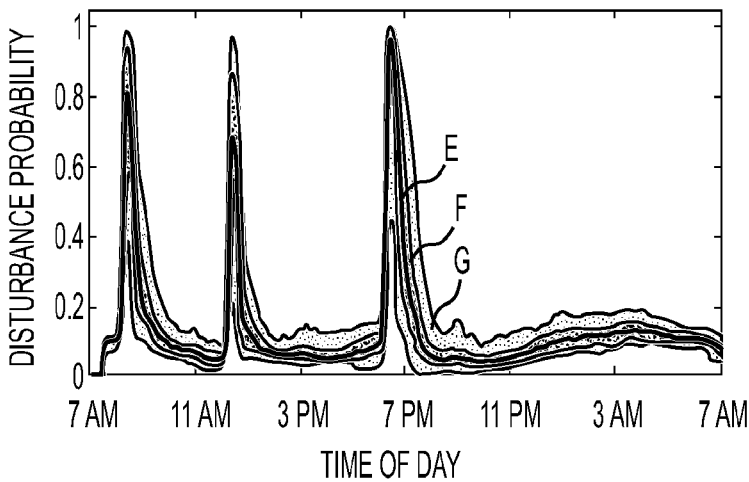
FIG. 7 illustrates an evolution of the probability of glycemic disturbance relative to administration of separate meals to the entire cohort of the in silico study.

In a second scenario, three meals of 50 g, 50 g, and 80 g carbohydrates were administered at 8 a.m., 12 m., and 6 p.m., respectively, to the whole adult cohort of the UVA/Padova simulator. In referring to FIG. 7, there is shown the time evolution of the disturbance probability for the three meals, in which median values are depicted at "E," 25%-75% ranges are depicted at "F," and 5%-95% ranges are depicted at "G."

C) Clinical Trial Simulation

Figure 8:
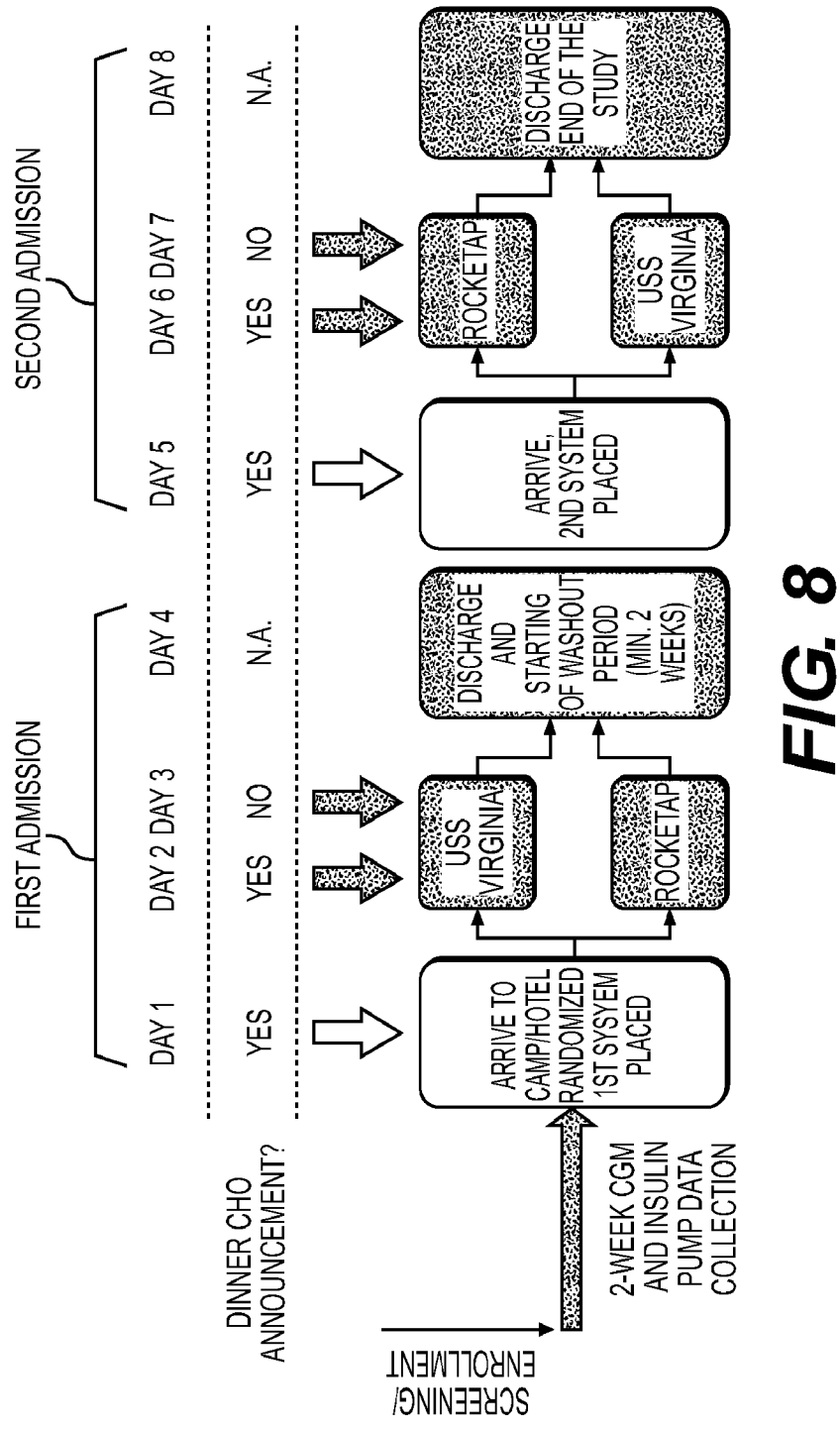
FIG. 8 illustrates a timeline for the in silico study.

The simulation protocol was designed to mimic the in-vivo clinical trial (NCT04545567, ClinicalTrials.gov). The simulation results evaluated the performance of the controller during experimental treatment as against the baseline treatment, assuming perfect functioning of the hardware. Participants were randomized to be on Rocket AP or USS Virginia as shown in FIG. 8, and which further illustrates the study timeline. Therein, participants were engaged in real-life activities on days 2, 3, 6, and 7, while being randomized among the two controllers (e.g., Rocket AP in days 2 and 3 and USS Virginia 2 in days 3 and 4, or, vice versa according to randomization). During the four days of each of the first and second admission, participants consumed three structured meals at 8 a.m., 12 m. and 6 p.m. every day with identical protein, fat, and carbohydrate content between study sessions. Carbohydrate contents of 50 g, 50 g, and for breakfast, lunch, and dinner, respectively, were implemented. On days 2 and 6, all meals were announced to the controllers. On days 3 and 7, breakfast and lunch were announced while dinner was not announced.

Figure 9A:
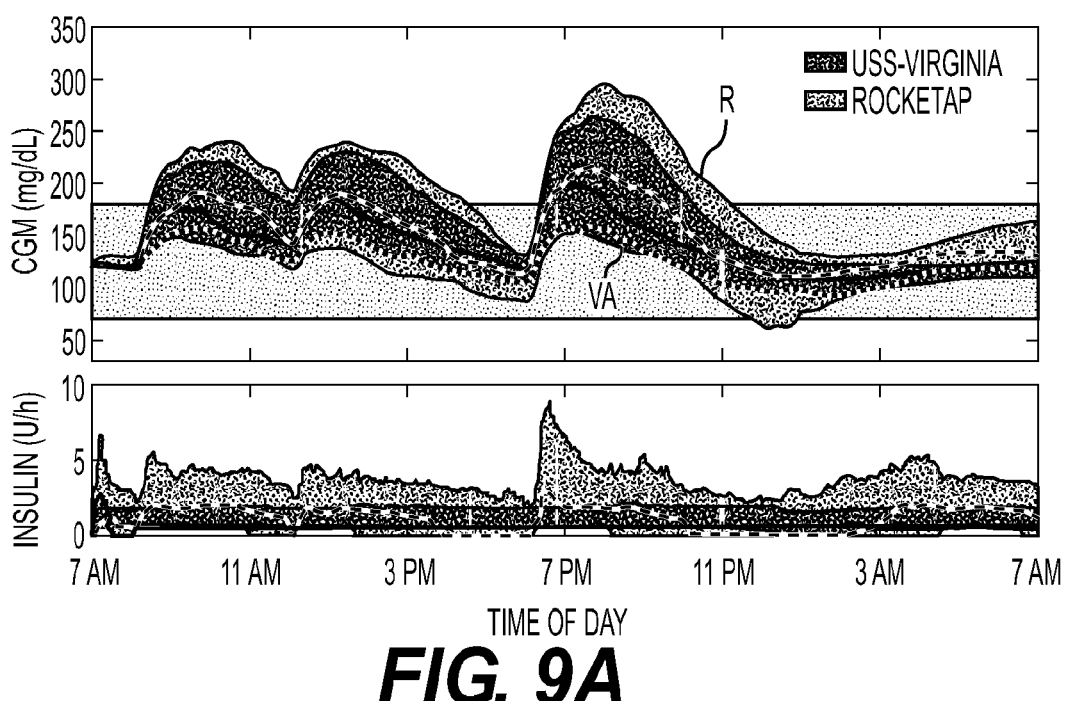
FIGS. 9A and 9B illustrate glucose readings for the entire cohort of the in silico study relative to delivered insulin.
Figure 9B:
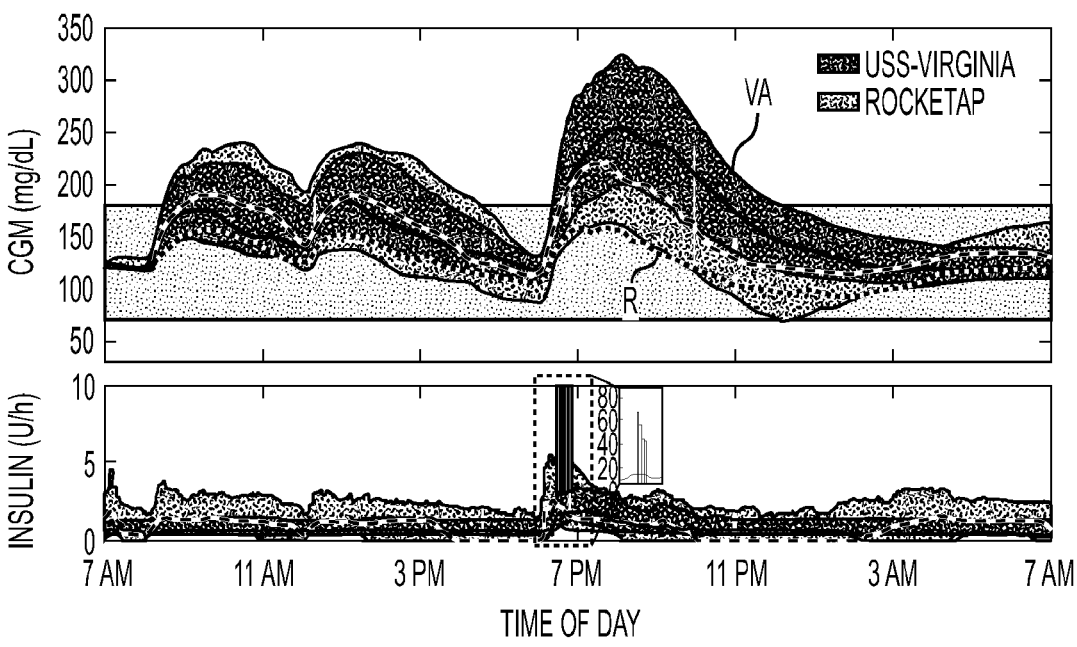

FIGS. 9A and 9B show a relative comparison of Rocket AP (R) as against USS Virginia (VA) as to the median and 5-95 percentile range of the CGM for the entire adult cohort for "all meals announced" and "dinner unannounced" admission days, respectively (in which envelopes represent the range, solid lines represent median values and insulin is basal insulin). Tables 6 and 7 below show the CGM-related metrics for both admission days according to international standards.[44] Particularly, percent TIR or percent time spent in euglycemia [70-180] mg/dL, percent time in hypoglycemia (<70 mg/dL), and percent time in hyperglycemia (>180 mg/dL) were examined. Low Blood Glucose Index (LBGI) and High Blood Glucose Index (HBGI) were computed according to B. P. Kovatchev.[51]

TABLE 6

| CGM metric | Overall | | | Overnight | | |
| --- | --- | --- | --- | --- | --- | --- |
| | Control-IQ | RocketAP | p-value | Control-IQ | RocketAP | p-value |
| Mean BG (mg/dL) | 141.0[134.7-148.5] | 149.2[143.6-159.4] | <0.001† | 113.2[111.0-115.7] | 122.0[117.4-126.7] | <0.001† |
| % time <54 mg/dL | 0[0-0] | 0[0-0] | 0.063† | 0[0-0] | 0[0-0] | 0.063† |
| % time <70 mg/dL | 0[0-0] | 0[0-0] | 0.008† | 0[0-0] | 0[0-0] | 0.008† |
| % time [70-140] mg/dL | 53.6[47.1-64.4] | 49.7[42.1-57.0] | <0.001† | 100[100-100] | 90.6[76.7-100] | <0.001† |
| % time [70-180] mg/dL | 87.8[78.5-97.4] | 75.7[66.7-85.7] | <0.001† | 100[100-100] | 100[100-100] | <0.001† |
| % time >180 mg/dL | 12.2[2.6-21.5] | 23.7[14.3-32.2] | <0.001† | 0[0-0] | 0[0-0] | 0.023† |
| % time >250 mg/dL | 0[0-0] | 0[0-2.8] | <0.001† | 0[0-0] | 0[0-0] | <0.001† |
| % CV-glucose | 20.1 ± 5.8 | 24.8 ± 5.9 | <0.001* | 5.0[3.5-7.8] | 10.2[7.3-14.3] | <0.001† |
| SD-glucose (mg/dL) | 28.8[21.3-34.9] | 37.6[30.2-44.6] | <0.001† | 5.6[3.9-8.7] | 12.7[8.9-18.5] | <0.001† |
| LBGI | 1.5[0.0015-0.035] | 0.016[0.0016-0.13] | <0.001† | 0.049[0.0052-0.12] | 0.10[0.073-0.14] | <0.001† |
| HBGI | 2.80[1.78-4.09] | 4.25[3.16-5.82] | <0.001† | 0.06[0.129-0.14] | 0.57[0.37-0.88] | <0.001† |

| CGM metric | Postprandial | | |
| --- | --- | --- | --- |
| | Control-IQ | RocketAP | p-value |
| Mean BG (mg/dL) | 155.8[146.2-168.3] | 171.9[154.3-188.9] | <0.001† |
| % time <54 mg/dL | 0[0-0] | 0[0-0] | 0.25† |
| % time <70 mg/dL | 0[0-0] | 0[0-0] | 0.016† |
| % time [70-140] mg/dL | 36.3[24.7-48.5] | 29.4[15.2-39.9] | <0.001† |
| % time [70-180] mg/dL | 75.2[60.1-91.3] | 52.8[41.0-70.4] | <0.001† |
| % time >180 mg/dL | 24.8[8.7-39.9] | 46.0[29.5-59.0] | <0.001† |
| % time >250 mg/dL | 0[0-0] | 0[0-5.5] | <0.001† |
| % CV-glucose | 18.6 ± 6.2 | 22.8 ± 6.4 | <0.001* |
| SD-glucose (mg/dL) | 30.0 ± 11.8 | 39.4 ± 12.7 | <0.001* |
| LBGI | 0[0-0.0027] | 0.0037[0-0.071] | <0.001† |
| HBGI | 4.58[2.96-6.67] | 7.64[4.77-10.93] | <0.001† |

SD and CV stand for Standard Deviation and Coefficient of Variation, respectively.

Values are shown as mean ± SD for normally distributed samples and median [IQR] for non-normally distributed samples.

Significance levels <0.05 are presented in bold font.

*One-sided paired t-test;

†Wilcoxon signed-rank test

TABLE 7

| CGM metric | Overall | | | Overnight | | |
|---|---|---|---|---|---|---|
| | Control-IQ | RocketAP | p-value | Control-IQ | RocketAP | p-value |
| Mean BG (mg/dL) | 157.6[148.6-164.5] | 149.2[143.4-158.2] | <0.001† | 127.6[121.6-135.5] | 121.7[116.9-125.8] | <0.001† |
| % time <54 mg/dL | 0[0-0] | 0[0-0] | 0.50† | 0[0-0] | 0[0-0] | 0.50† |
| % time <70 mg/dL | 0[0-0] | 0[0-0] | 0.03† | 0[0-0] | 0[0-0] | 0.03† |
| % time [70-140] mg/dL | 44.3 ± 11.4 | 50.2 ± 9.4 | <0.001† | 78.1[68.1-90.3] | 93.2[79.9-100] | <0.001† |
| % time [70-180] mg/dL | 77.4[69.4-82] | 76.1[67.0-86.0] | 0.11† | 100[96.2-100] | 100[100-100] | 0.007† |
| % time >180 mg/dL | 22.6[15.8-30.6] | 23.8[14.0-31.6] | 0.03† | 0[0-3.8] | 0[0-0] | <0.001† |
| % time >250 mg/dL | 3.3[0-8.3] | 0[0-3.6] | <0.001† | 0[0-0] | 0[0-0] | 1.00† |
| % CV-glucose | 25.5 ± 5.4 | 25.0 ± 5.8 | 0.07* | 10.8[7.5-14.6] | 9.7[7.2-14.1] | 0.96† |
| SD-glucose (mg/dL) | 40.1[33.5-46.2] | 37.0[30.3-44.3] | <0.001* | 13.8[10.4-19.4] | 12.1[8.8-17.2] | 0.07† |
| LBGI | 0[0-0.0017] | 0.021[0.0021-0.12] | <0.001† | 0[0-0.001] | 0.023[0-0.18] | <0.001† |
| HBGI | 5.22[3.93-6.25] | 4.20[3.15-5.74] | <0.001† | 1.09[0.46-1.87] | 0.55[0.35-0.82] | <0.001† |

| CGM metric | Postprandial | | |
|---|---|---|---|
| | Control-IQ | RocketAP | p-value |
| Mean BG (mg/dL) | 205.1 ± 22.4 | 171.8 ± 24.9 | <0.001* |
| % time <54 mg/dL | 0[0-0] | 0[0-0] | 1.00† |
| % time <70 mg/dL | 0[0-0] | 0[0-0] | 0.06† |
| % time [70-140] mg/dL | 6.1[4.6-11.8] | 32.3[17.9-42.4] | <0.001† |
| % time [70-180] mg/dL | 33.1 ± 15.1 | 58.3 ± 20.5 | <0.001* |
| % time >180 mg/dL | 66.9 ± 15.1 | 41.3 ± 21.0 | <0.001* |
| % time >250 mg/dL | 13.2[0-33.1] | 0[0-13.7] | <0.001† |
| % CV-glucose | 19.9 ± 5.2 | 24.0 ± 6.8 | <0.001* |
| SD-glucose (mg/dL) | 41.3 ± 12.9 | 41.3 ± 13.2 | 0.50* |
| LBGI | 0[0-0] | 0.0062[0-0.078] | <0.001† |
| HBGI | 13.18[10.25-15.90] | 7.49[4.73-10.51] | <0.001† |

SD and CV stand for Standard Deviation and Coefficient of Variation, respectively.
Values are shown as mean ± SD for normally distributed samples and median [IQR] for non-normally distributed samples.
Significance levels <0.05 are presented in bold font.
*One-sided paired t-test;
†Wilcoxon signed-rank test As may be appreciated from FIGS. 9A and 9B and the above tables, Rocket AP outperformed USS Virginia following the unannounced (dinner) in terms of percent TIR and percent time >180 mg/dL.

Figure 10A:
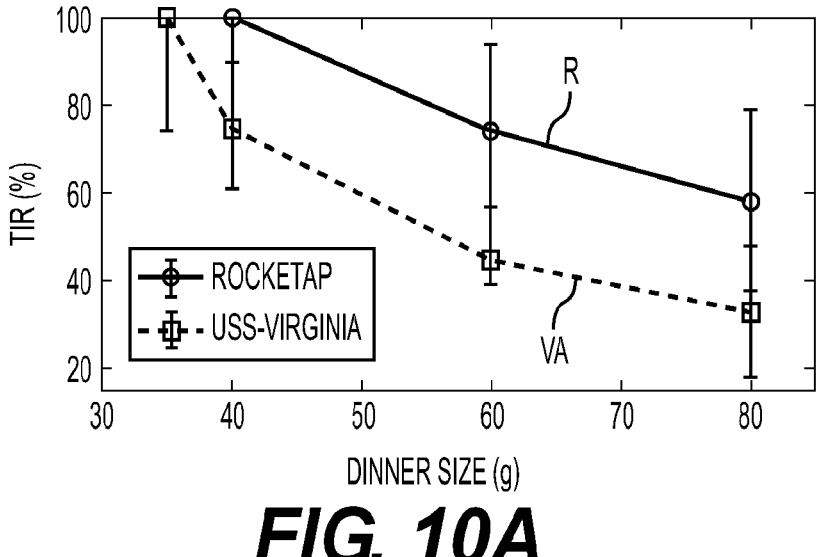
FIGS. 10A and 10B illustrate error plots demonstrating time in range (TIR) and time beyond range in a six (6) hour window following varying meal size, relative to the MPC according to embodiments herein as against legacy control.
Figure 10B:
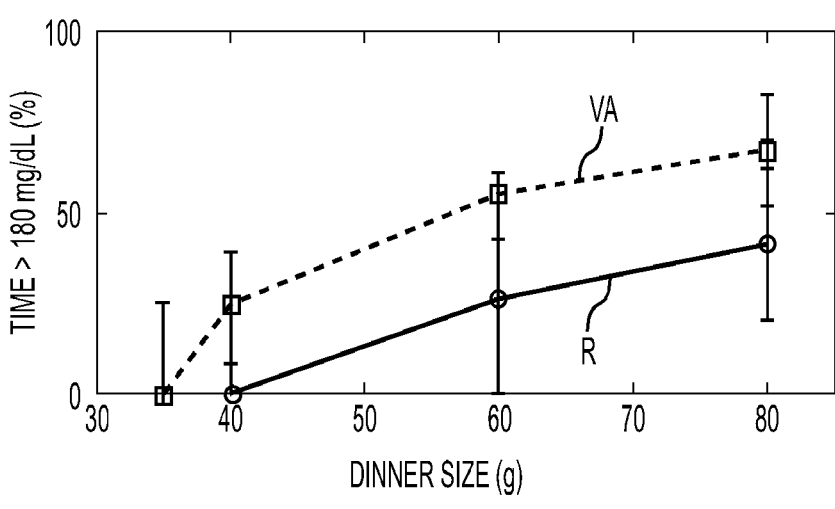

Finally, we explored the performance of both Rocket AP and USS Virginia after various, hypothetical unannounced meals with different carbohydrate loads ranging from 5 g to 80 g of carbohydrates. Both systems exhibited robustness to meal challenges of less than 30 g of carbohydrates in the six (6) hours following the meal (percent time in range 100 [100-100] %. In referring to FIGS. 10A and 10B respectively showing error plots for median and IQR of the percent TIR and percent time >180 mg/dL for Rocket AP (R) and USS Virginia (VA) for carbohydrate values ranging from 35 g to 80 g in the six (6) hours following such meals. Percent time <70 mg/dL was 0 [0-0] % for both controllers. Thus, as expected, the percent TIR decreases with increasing carbohydrate content, thereby translating the percentage loss into percent time >180 mg/dL.

In Vivo Study

Relative to the above reported clinical study examining 18 study participants who completed the study and were aged 12-20 years, we found that the Rocket AP controller of FIG. 1, when compared to the commercially available USS Virginia, performed similarly as in the in silico study with respect to TIR and percentile of time <70 mg/dL. This was true of instances of unannounced dinner glycemic outcomes and overall outcomes.

In regard to unannounced dinners, TIR for the six (6) hour period after the unannounced dinner (primary outcome) was significantly higher for the Rocket AP controller RCKT than with USS Virginia (83% [64-93] vs. 53% [40-71]; p=0.004), see Table 8 below. Time in Tight Range (TTR) or 80-140 mg/dL was also higher (49% [41-59] vs. 27% [22-36]; p=0.002). Mean CGM and percentile of time>180 mg/dL were significantly lower for the Rocket AP controller (141±21 mg/dL vs. 166±26 mg/dL; p=0.001) and (17% [1.3-34] vs. 47% [28-60]; p=0.01), respectively (see Table 1). Improvements in glycemia with respect to the Rocket AP controller extended in the 12-hour period after the unannounced dinner. In terms of announcement of the dinner meal, the Rocket AP controller further outperformed the USS Virginia as to these study participants, providing a point of difference with regard to the in silico study discussed herein.

TABLE 8

| | Unannounced dinner (primary outcome) | | | Announced dinner (Secondary outcome) | | |
|---|---|---|---|---|---|---|
| | USS | RCKT | P-value | USS | RCKT | P-value |
| Glycemic metrics | | | | | | |
| Mean CGM glucose (mg/dL) | 166 ± 26 | 141 ± 21 | 0.001ᵃ | 114 ± 26 | 114 ± 11 | 0.45 |
| % CGM time < 50 mg/dL (<2.8 mmol/L) | 0 [0-0] | 0 [0-0] | 1 | 0 [0-0] | 0 [0-0] | 1 |
| % CGM time < 60 mg/dL (<3.3 mmol/L) | 0 [0-0] | 0 [0-0] | 0.5 | 0 [0-0] | 0 [0-0] | 0.08 |
| % CGM time < 70 mg/dL (<3.9 mmol/L) | 0 [0-0] | 0 [0-1] | 0.2 | 0.7 [0-8] | 0 [0-0] | 0.04ᵇ |

TABLE 8-continued

| | Unannounced dinner (primary outcome) | | | Announced dinner (Secondary outcome) | | |
|---|---|---|---|---|---|---|
| | USS | RCKT | P-value | USS | RCKT | P-value |
| % CGM time 70-140 mg/dL (3.9-7.8 mmol/L) | 27 [22-36] | 49 [41-59] | 0.002[b] | 82 [57-89] | 86 [69-94] | 0.13 |
| % CGM time 70-180 mg/dL (3.9-10.0 mmol/L) | 53 [40-71] | 83 [64-93] | 0.004[b] | 93 [85-99] | 100 [99-100] | 0.004[b] |
| % CGM time > 180 mg/dL (>10.0 mmol/L) | 47 [28-60] | 17 [1.3-34] | 0.01[b] | 0 [0-1] | 0 [0-0] | 0.10 |
| % CGM time > 250 mg/dL (>13.9 mmol/L) | 0 [0-0] | 0 [0-0] | 1 | 0 [0-0] | 0 [0-0] | 1 |
| % CGM time > 300 mg/dL (>16.7 mmol/L) | 0 [0-0] | 0 [0-0] | 1 | 0 [0-0] | 0 [0-0] | 1 |
| CGM SD (mg/dL) | 40 ± 13 | 37 ± 17 | 0.2 | 20 ± 8.5 | 23 ± 7 | 0.11 |
| CGM CV (%) | 24 ± 9 | 26 ± 9 | 0.4 | 17.5 ± 7.1 | 20 ± 6 | 0.10 |
| Safety metrics | | | | | | |
| Severe hypoglycemia (number of events) | 0 [0-0] | 0 [0-0] | 1[b] | 0 [0-0] | 0 [0-0] | 1[b] |
| Diabetes ketoacidosis (number of events) | 0 [0-0] | 0 [0-0] | 1[b] | 0 [0-0] | 0 [0-0] | 1[b] |
| Technical performance metrics | | | | | | |
| Percent time in CLC (%) | 95 ± 15 | 100 ± 1 | 0.16 | 92 ± 17 | 99 ± 2 | 0.16 |
| Total injected insulin (IU) | 14 ± 4 | 15 ± 5 | 0.21 | 14 ± 4 | 15 ± 7 | 0.22 |

Overall control during about 46 hours revealed that Rocket AP achieved higher TTR and TIR (72.3%±7.9 vs. 63.7%±13; p=0.01; and 87%±6.6 vs. 80%±9.6; p=0.007), respectively) and lower mean BG and percentile of time>180 mg/dL (122±7.5 mg/dL vs. 128±15.5 mg/dL, p=0.05; and 9.4±5.6% vs. 13.4±8.7%, p=0.03, respectively (see Table 9 below). Baseline control per USS Virginia showed an increase in TIR for [15]/[18] participants relative to [17]/[18] participants per Rocket AP.

TABLE 9

| | Unannounced dinner (Secondary outcomes) | | | Announced dinner (Secondary outcomes) | | |
|---|---|---|---|---|---|---|
| | USS | RCKT | P-value | USS | RCKT | P-value |
| Glycemic metrics | | | | | | |
| Mean CGM glucose (mg/dL) | 145 ± 25 | 123 ± 11 | <0.001[a] | 116.5 ± 20 | 110.2 ± 7.5 | 0.1 |
| % CGM time < 50 mg/dL (<2.8 mmol/L) | 0 [0-0] | 0 [0-0] | 1 | 0 [0-0] | 0 [0-0] | 1 |
| % CGM time < 60 mg/dL (<3.3 mmol/L) | 0 [0-0] | 0 [0-0] | 0.26 | 0 [0-0] | 0 [0-0] | 0.08 |
| % CGM time < 70 mg/dL (<3.9 mmol/L) | 0 [0-0.7] | 0 [0-1.2] | 0.54 | 0.7 [0-4.9] | 0 [0-2] | 0.14 |
| % CGM time 70-140 mg/dL (3.9-7.8 mmol/L) | 52 [42-64] | 73 [70-76] | 0.004[b] | 83 [56-90] | 89 [78-96] | 0.03[b] |
| % CGM time 70-180 mg/dL (3.9-10.0 mmol/L) | 75 [58-83] | 90 [79-95] | <0.001[b] | 95 [91-99] | 100 [97-100] | 0.007[b] |
| % CGM time > 180 mg/dL (>10.0 mmol/L) | 25 [14-37] | 8.7 [3-17] | 0.003[b] | 0 [0-1.2] | 0 [0-0] | 0.11 |
| % CGM time > 250 mg/dL (>13.9 mmol/L) | 0 [0-0] | 0 [0-0] | 0.52 | 0 [0-0] | 0 [0-0] | 1 |
| % CGM time > 300 mg/dL (>16.7 mmol/L) | 0 [0-0] | 0 [0-0] | 1 | 0 [0-0] | 0 [0-0] | 1 |
| CGM SD (mg/dL) | 41 ± 9.2 | 35 ± 14 | 0.06 | 23 ± 8 | 21 ± 6.3 | 0.25 |
| CGM CV (%) | 29 ± 6.5 | 29 ± 11 | 0.56 | 20 ± 5 | 19 ± 6 | 0.32 |
| Safety metrics | | | | | | |
| Severe hypoglycemia (number of events) | 0 [0-0] | 0 [0-0] | 1[b] | 0 [0-0] | 0 [0-0] | 1[b] |
| Diabetes ketoacidosis (number of events) | 0 [0-0] | 0 [0-0] | 1[b] | 0 [0-0] | 0 [0-0] | 1[b] |
| Technical performance metrics | | | | | | |
| Percent time in CLC (%) | 97 ± 7 | 100 ± 1 | 0.16 | 93 ± 14 | 100 ± 2 | 0.14 |
| Total injected insulin (IU) | 20 ± 4 | 21 ± 6 | 0.28 | 17.5 ± 5 | 17 ± 5 | 0.33 |

As shown below in Table 10, the Rocket AP controller achieved significant tight control, TTR, overnight when compared to USS Virginia (95.3 [90.4-100] % vs. 76.3 [58.5-87.4] %, p<0.001), as well as TIR (99.2 [95.7-100] % vs. 92.2 [81.2-96] %, p<0.001) and mean BG (106.4±7.3 mg/dL vs. 123±20 mg/dL; p=0.002).

TABLE 10

| Secondary outcomes | | | |
| --- | --- | --- | --- |
| | USS | RCKT | P-value |
| Glycemic metrics | | | |
| Mean CGM glucose (mg/dL) | 123 ± 20 | 106.4 ± 7.3 | $0.002^a$ |
| % CGM time <50 mg/dL (<2.8 mmol/L) | 0 [0-0] | 0 [0-0] | 1 |
| % CGM time <60 mg/dL (<3.3 mmol/L) | 0 [0-0] | 0 [0-0] | 0.26 |
| % CGM time <70 mg/dL (<3.9 mmol/L) | 0 [0-3.8] | 0 [0-3.7] | 0.47 |
| % CGM time 70-140 mg/dL (3.9-7.8 mmol/L) | 76.3 [58.5-87.4] | 95.3 [90.4-100] | $<0.001^b$ |
| % CGM time 70-180 mg/dL (3.9-10.0 mmol/L) | 92.2 [81.2-96] | 99.2 [95.7-100] | $<0.001^b$ |
| % CGM time >180 mg/dL (>10.0 mmol/L) | 5 [0-9.8] | 0 [0-0] | $0.002^b$ |
| % CGM time >250 mg/dL (>13.9 mmol/L) | 0 [0-0] | 0 [0-0] | 1 |
| % CGM time >300 mg/dL (>16.7 mmol/L) | 0 [0-0] | 0 [0-0] | 1 |
| CGM SD (mg/dL) | 28 ± 9.7 | 18.1 ± 7.2 | $0.004^a$ |
| CGM CV (%) | 22 ± 5.7 | 7 ± 7 | $0.01^a$ |
| Safety metrics | | | |
| Severe hypoglycemia (number of events) | 0 [0-0] | 0 [0-0] | 1 |
| Diabetes ketoacidosis (number of events) | 0 [0-0] | 0 [0-0] | 1 |
| Technical performance metrics | | | |
| Percent time in CLC (%) | 96 ± 7 | 99 ± 2 | 0.07 |
| Total injected insulin (IU) | 15 ± 4 | 14 ± 5 | 0.34 |

30

When compared to the in silico study addressed herein and exemplifying performance of the Rocket AP for an adult cohort, the above in vivo results further buttress the integrity of such performance since the focus was placed on an adolescent population, which is notorious for not announcing meal intake.[52-54]

In view of the above, it will be appreciated that we have disclosed a dual mode CLC system integrating each of (i) an adaptive personalized MPC control law that modulates the control strength of insulin infusion depending on recent past control actions, glucose measurements, and their derivative(s), (ii) an automatic BPS that commands additional insulin injections safely upon the detection of enabling metabolic conditions (e.g., an unannounced meal), and (iii) a HMS to avoid prevailing hyperglycemia.

Figure 11:
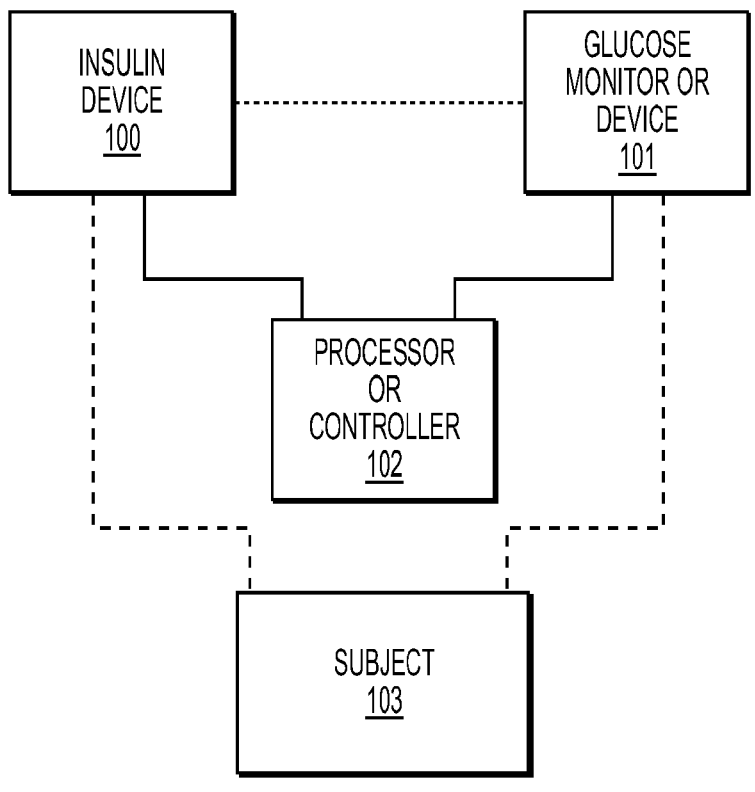
FIG. 11 illustrates an exemplary construct for the CLC of embodiments herein.

In referring to FIG. 11, a processor or controller 102, as embodied, for instance, by a DiA, communicates with the glucose monitor or device 101, and optionally the insulin device 100. The processor or controller 102, as embodied by the DiA, may be configured to include all necessary hardware and/or software necessary to perform any and all required instructions, or portions thereof, to achieve the aforementioned tasks discussed herein, e.g., bolus calculation. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 may be implemented locally in the glucose monitor 101, the insulin device 100, or a standalone device (or in any combination of two or more of the glucose monitor, insulin device, or a standalone device). The processor 102 or a portion of the system may be located remotely such that the device is operated as a telemedicine device.

Figure 12A:
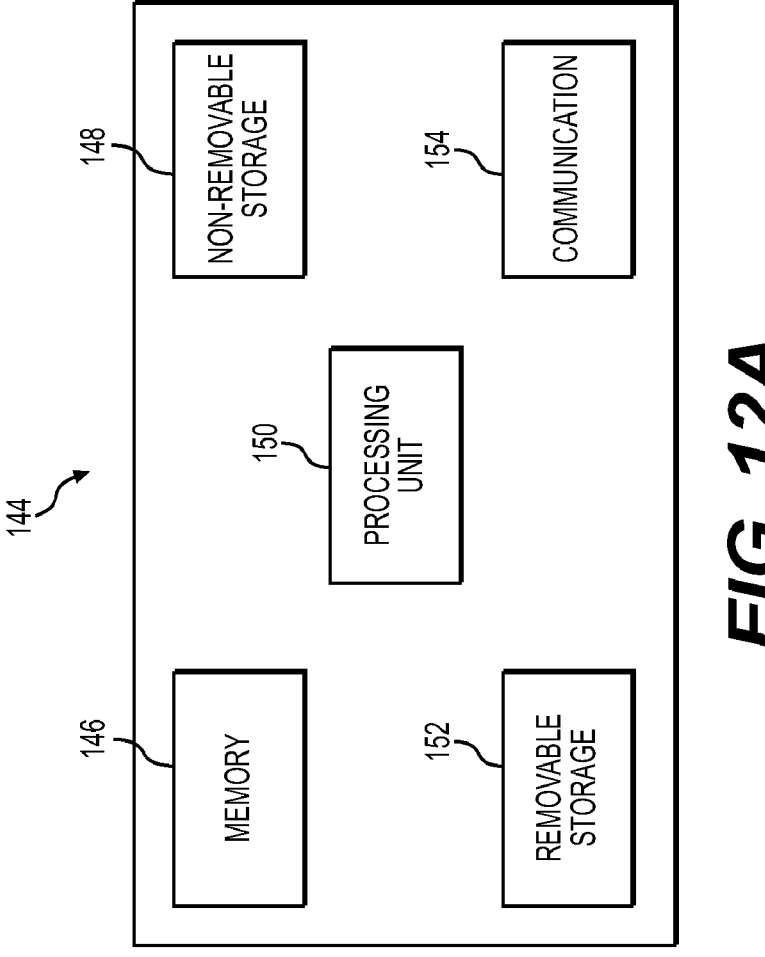
FIG. 12A illustrates an exemplary computing device which may implement one or more portions of the CLC of embodiments herein.

In referring to FIG. 12A, in its most basic configuration, computing device 144, optionally implementing the DiA, typically includes at least one processing unit 150 and memory 146. Depending on the exact configuration and type of computing device, memory 146 may be volatile (such as RANI), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which may be used to store the desired information and which may accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 12B:
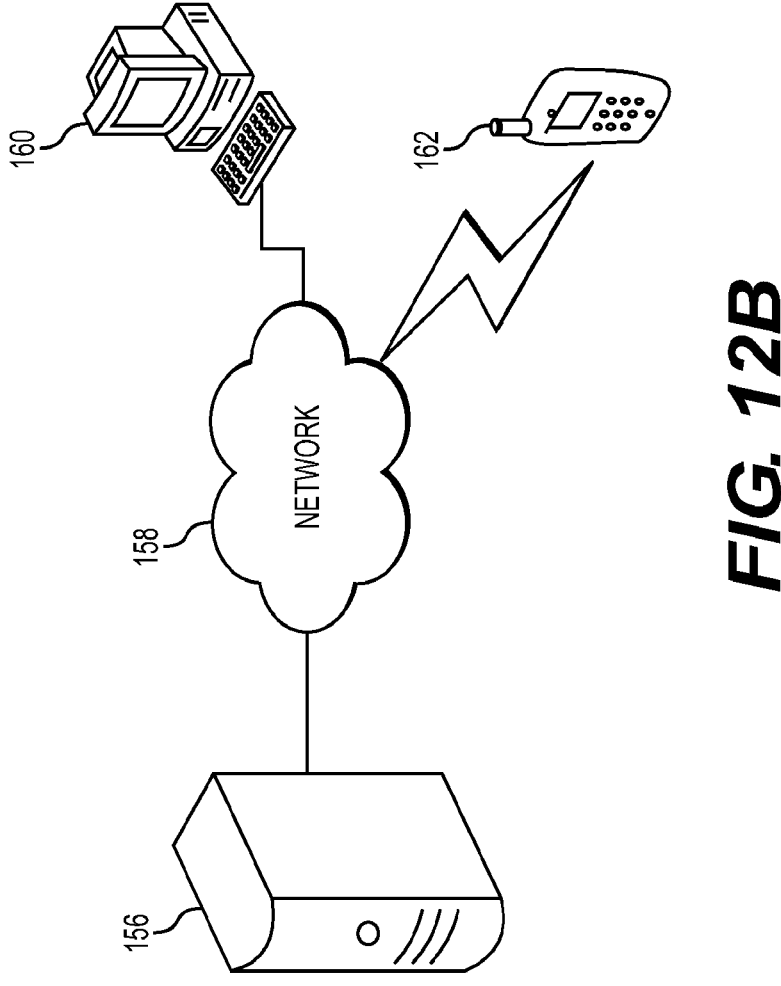
FIG. 12B illustrates a network system which may implement and/or be used in the implementation of one or more portions of the CLC of embodiments herein.

In referring to FIG. 12B, embodiments herein may also be implemented on a network system comprising a plurality of computing devices that are in communication with a networking means, such as a network with an infrastructure or an ad hoc network. The network connection may be wired connections or wireless connections. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non-portable devices) with combinations of such features). In an embodiment, it should be appreciated that the module listed as 156 may be glucose monitor device. In an embodiment, it should be appreciated that the module listed as 156 may be a glucose monitor device, artificial pancreas, and/or an insulin device (or other interventional or diagnostic device). Any of the components shown or discussed with FIG. 12B may be multiple in number. The embodiments herein may be implemented in anyone of the devices of the system. For example, execution of the instructions or other desired processing may be performed on the same computing device that is anyone of 156, 160, and 162. Alternatively, an embodiment may be performed on different computing devices of the network system. For example, certain desired or required processing or execution may be performed on one of the computing devices of the network (e.g. server 156 and/or glucose monitor device), whereas other processing and execution of the instruction may be performed at another computing device (e.g. terminal 160) of the network system, or vice versa. In fact, certain processing or execution may be performed at one computing device (e.g. server 156 and/or insulin device, AP, or glucose monitor device (or other interventional or diagnostic device)); and the other processing or execution of the instructions may be performed at different computing devices that may or may not be networked. For example, the certain processing may be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected may be executed, encoded or processed with one or more embodiments herein. The processed, encoded or executed software may then be distributed to customers. The distribution may be in a form of storage media (e.g. disk) or electronic copy.

Figure 13:
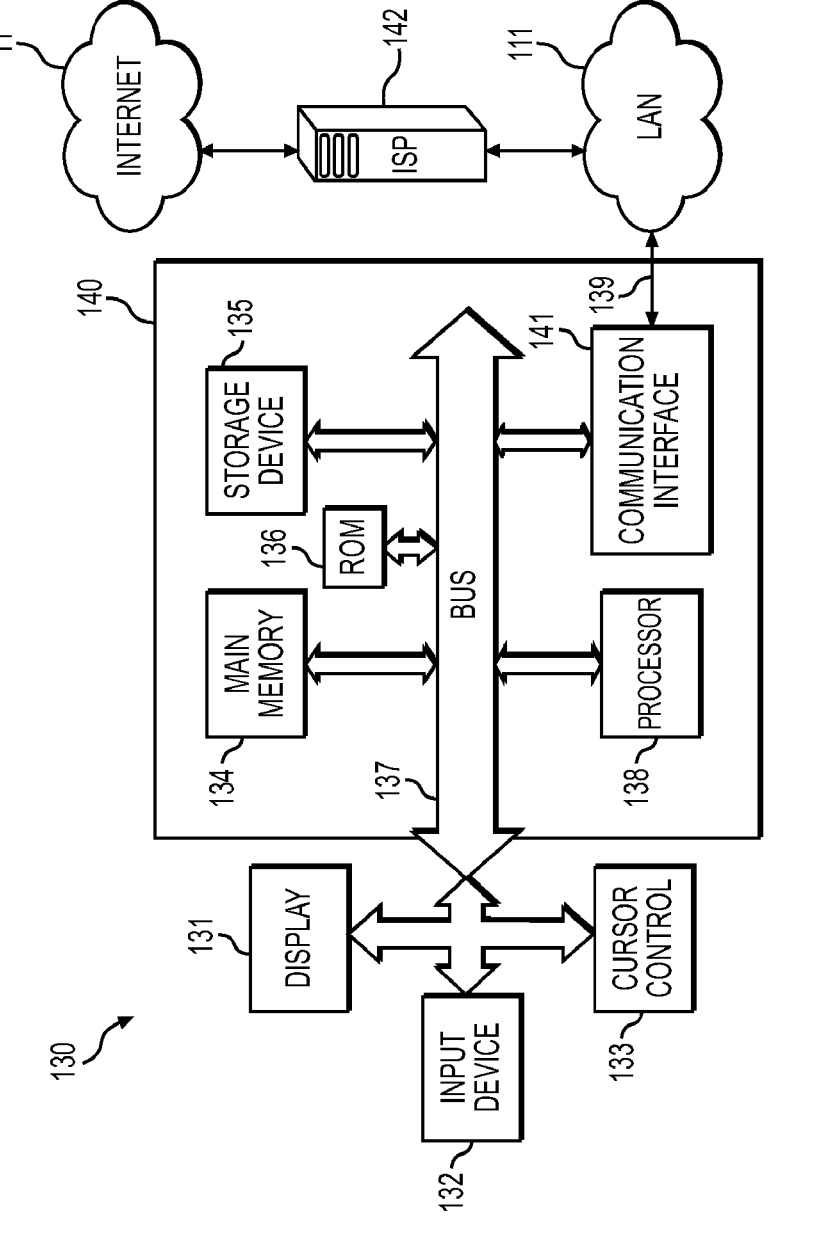
FIG. 13 illustrates a block diagram which may implement and/or be used in the implementation of one or more portions of the CLC herein in association with a connection to the Internet.

In referring to FIG. 13, there is shown a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 13. The system 140 may be used as a portable electronic device such as a notebook/laptop computer, a media player (e.g., MP3 based or video player), a cellular phone, a Personal Digital Assistant (PDA), a glucose monitor device, an artificial pancreas, an insulin delivery device (or other interventional or diagnostic device), an image processing device (e.g., a digital camera or video recorder), and/or any other handheld computing devices, or a combination of any of these devices. Note that while FIG. 13 illustrates various components of a computer system, it is not intended to represent any particular architecture or manner of interconnecting the components; as such details are not germane to the embodiments herein. It will also be appreciated that network computers, handheld computers, cell phones and other data processing systems which have fewer components or perhaps more components may also be used. The computer system of FIG. 13 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RANI) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically, computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments herein are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media may also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer may read.

Various forms of computer-readable media may be involved in carrying one or more sequences of one or more instructions to processor 138 for execution. For example, the instructions may initially be carried on a magnetic disk of a remote computer. The remote computer may load the instructions into its dynamic memory and send the instructions over a telephone line using a modem. A modem local to computer system 140 may receive the data on the telephone line and use an infra-red transmitter to convert the data to an infra-red signal. An infra-red detector may receive the data carried in the infra-red signal and appropriate circuitry may place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the worldwide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of a personalized artificial pancreas system with an automatic BPS and enhanced safety by the present inventors. As seen from the algorithm and methodology requirements discussed herein, the procedure is readily applicable into devices, such as glucose devices, insulin devices, AP devices, and other interventional or diagnostic devices, and may be implemented and utilized with the related processors, networks, computer systems, internet, and components and functions according to the schemes disclosed herein.

Figure 14:
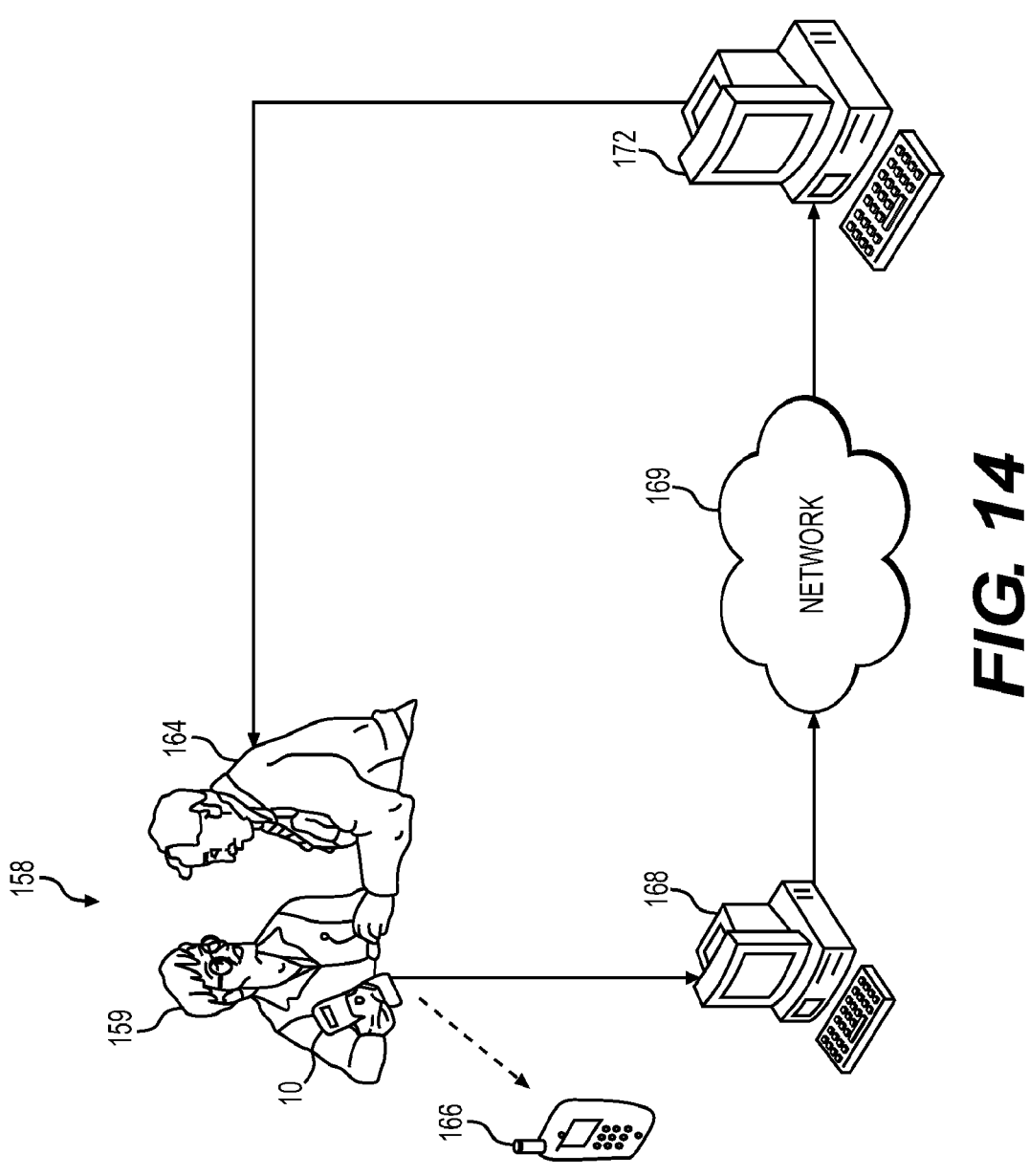
FIG. 14 illustrates a system which may implement and/or be used in the implementation of one or more portions of the CLC herein in accordance with one or more of a clinical setting and a connection to the Internet.

In referring to FIG. 14, there is illustrated a system in which one or more embodiments herein may be implemented using a network, or portions of a network or computers, although the presently discussed glucose monitor, AP or insulin device (or other interventional or diagnostic device) may be practiced without a network.

FIG. 14 diagrammatically illustrates an exemplary system in which examples of the embodiments herein may be implemented. In an embodiment the glucose monitor, AP or insulin device (or other interventional or diagnostic device) may be implemented by the subject (or patient) locally at home or other desired location. However, in an alternative embodiment it may be implemented in a clinic setting or assistance setting. For instance, referring to FIG. 14, a clinic setup 158 provides a place for doctors (e.g. 164) or clinician/assistant to diagnose patients (e.g. 159) with diseases related with glucose and related diseases and conditions. A glucose monitoring device 10 may be used to monitor and/or test the glucose levels of the patient—as a standalone device. It should be appreciated that while only glucose monitor device 10 is shown in the figure, the system of the embodiments herein and any component thereof may be used in the manner depicted by FIG. 14. The system or component may be affixed to the patient or in communication with the patient as desired or required. For example the system or combination of components thereof—including a glucose monitor device 10 (or other related devices or systems such as a controller, and/or an artificial pancreas, an insulin pump (or other interventional or diagnostic device), or any other desired or required devices or components)—may be in contact, communication or affixed to the patient through tape or tubing (or other medical instruments or components) or may be in communication through wired or wireless connections. Such monitor and/or test may be short term (e.g. clinical visit) or long term (e.g. clinical stay or family). The glucose monitoring device outputs may be used by the doctor (clinician or assistant) for appropriate actions, such as insulin injection or food feeding for the patient, or other appropriate actions or modeling. Alternatively, the glucose monitoring device output may be delivered to computer terminal 168 for instant or future analyses. The delivery may be through cable or wireless or any other suitable medium. The glucose monitoring device output from the patient may also be delivered to a portable device, such as PDA 166. The glucose monitoring device outputs with improved accuracy may be delivered to a glucose monitoring center 172 for processing and/or analyzing. Such delivery may be accomplished in many ways, such as network connection 169, which may be wired or wireless.

In addition to the glucose monitoring device outputs, errors, parameters for accuracy improvements, and any accuracy related information may be delivered, such as to computer 168, and/or glucose monitoring center 172 for performing error analyses. This may provide a centralized accuracy monitoring, modeling and/or accuracy enhancement for glucose centers, due to the importance of the glucose sensors.

Examples of the embodiments herein may also be implemented in a standalone computing device associated with the target glucose monitoring device, artificial pancreas, and/or insulin device (or other interventional or diagnostic device). An exemplary computing device (or portions thereof) in which examples of the embodiments herein may be implemented is schematically illustrated in FIG. 12A.

Figure 15:
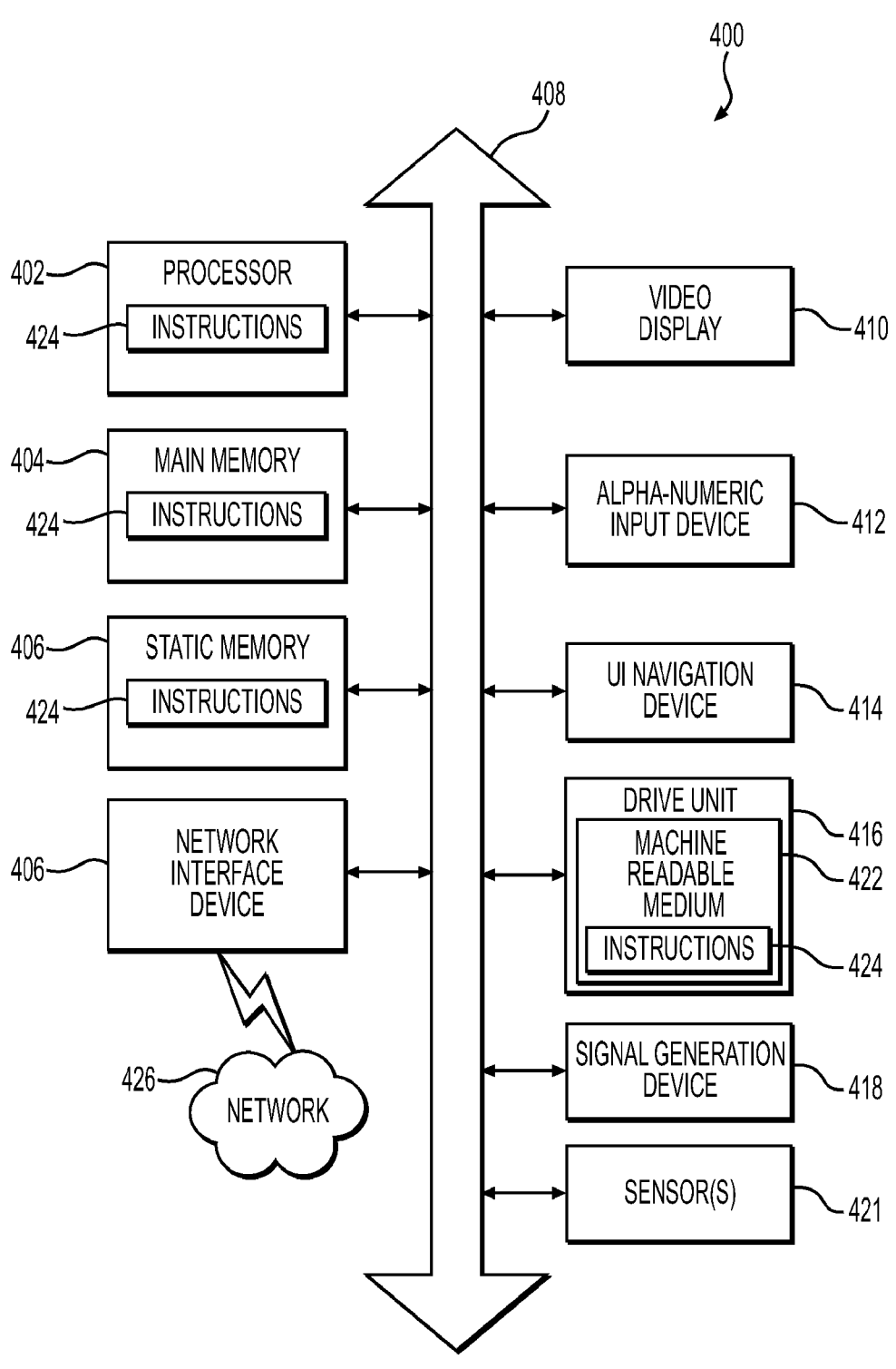
FIG. 15 illustrates an exemplary architecture embodying one or more portions of the CLC herein.

In referring to FIG. 15, there is shown a block diagram illustrating an example of a machine upon which one or more aspects of embodiments herein may be implemented.

FIG. 15 illustrates a block diagram of an example machine 400 upon which one or more embodiments (e.g., discussed methodologies) may be implemented (e.g., run).

Examples of machine 400 may include logic, one or more components, circuits (e.g., modules), or mechanisms. Circuits are tangible entities configured to perform certain operations. In an example, circuits may be arranged (e.g., internally or with respect to external entities such as other circuits) in a specified manner. In an example, one or more computer systems (e.g., a standalone, client or server computer system) or one or more hardware processors (processors) may be configured by software (e.g., instructions, an application portion, or an application) as a circuit that operates to perform certain operations as described herein. In an example, the software may reside (1) on a non-transitory machine readable medium or (2) in a transmission signal. In an example, the software, when executed by the underlying hardware of the circuit, causes the circuit to perform the certain operations.

In an example, a circuit may be implemented mechanically or electronically. For example, a circuit may comprise dedicated circuitry or logic that is specifically configured to perform one or more techniques such as discussed above, such as including a special-purpose processor, a field programmable gate array (FPGA) or an application-specific integrated circuit (ASIC). In an example, a circuit may comprise programmable logic (e.g., circuitry, as encompassed within a general-purpose processor or other programmable processor) that may be temporarily configured (e.g., by software) to perform the certain operations. It will be appreciated that the decision to implement a circuit mechanically (e.g., in dedicated and permanently configured circuitry), or in temporarily configured circuitry (e.g., configured by software) may be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor may be configured as respective different circuits at different times. Software may accordingly configure a processor, for example, to constitute a particular circuit at one instance of time and to constitute a different circuit at a different instance of time.

In an example, circuits may provide information to, and receive information from, other circuits. In this example, the circuits may be regarded as being communicatively coupled to one or more other circuits. Where multiple of such circuits exist contemporaneously, communications may be achieved through signal transmission (e.g., over appropriate circuits and buses) that connect the circuits. In embodiments in which multiple circuits are configured or instantiated at different times, communications between such circuits may be achieved, for example, through the storage and retrieval of information in memory structures to which the multiple circuits have access. For example, one circuit may perform an operation and store the output of that operation in a memory device to which it is communicatively coupled. A further circuit may then, at a later time, access the memory device to retrieve and process the stored output. In an example, circuits may be configured to initiate or receive communications with input or output devices and may operate on a resource (e.g., a collection of information).

The various operations of method examples described herein may be performed, at least partially, by one or more processors that are temporarily configured (e.g., by software) or permanently configured to perform the relevant operations. Whether temporarily or permanently configured, such processors may constitute processor-implemented circuits that operate to perform one or more operations or functions. In an example, the circuits referred to herein may comprise processor-implemented circuits.

Similarly, the methods described herein may be at least partially processor-implemented. For example, at least some of the operations of a method may be performed by one or more processors or processor-implemented circuits. The performance of certain of the operations may be distributed among the one or more processors, not only residing within a single machine, but deployed across a number of machines. In an example, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) may be implemented in digital electronic circuitry, in computer hardware, in firmware, in software, or in any combination thereof. Example embodiments may be implemented using a computer program product (e.g., a computer program, tangibly embodied in an information carrier or in a machine readable medium, for execution by, or to control the operation of, data processing apparatus such as a programmable processor, a computer, or multiple computers).

A computer program may be written in any form of programming language, including compiled or interpreted languages, and it may be deployed in any form, including as a stand-alone program or as a software module, subroutine, or other unit suitable for use in a computing environment. A computer program may be deployed to be executed on one computer or on multiple computers at one site or distributed across multiple sites and interconnected by a communication network.

In an example, operations may be performed by one or more programmable processors executing a computer program to perform functions by operating on input data and generating output. Examples of method operations may also be performed by, and example apparatus may be implemented as, special purpose logic circuitry (e.g., a field programmable gate array (FPGA) or an application-specific integrated circuit (ASIC)).

The computing system may include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine 400) and software architectures that may be deployed in example embodiments.

In an example, the machine 400 may operate as a stand-alone device or the machine 400 may be connected (e.g., networked) to other machines.

In a networked deployment, the machine 400 may operate in the capacity of either a server or a client machine in server-client network environments. In an example, machine 400 may act as a peer machine in peer-to-peer (or other distributed) network environments. The machine 400 may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 may include a processor 402 (e.g., a central processing unit (CPU), a graphics processing unit (GPU) or both), a main memory 404 and a static memory 406, some or all of which may communicate with each other via a bus 408. The machine 400 may further include a display unit 410, an alphanumeric input device 412 (e.g., a keyboard), and a user interface (UI) navigation device 411 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 may include a machine readable medium 422 on which is stored one or more sets of data structures or instructions 424 (e.g., software) embodying or utilized by any one or more of the methodologies or functions described herein. The instructions 424 may also reside, completely or at least partially, within the main memory 404, within static memory 406, or within the processor 402 during execution thereof by the machine 400. In an example, one or any combination of the processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) that configured to store the one or more instructions 424. The term "machine readable medium" may also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" may accordingly be taken to include, but not be limited to, solid-state memories, and optical and magnetic media. Specific examples of machine readable media may include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, IP, TCP, UDP, HTTP, etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g. rat, dog, pig, monkey), etc. It should be appreciated that the subject may be any applicable human patient, for example.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

In summary, while the present disclosure has been described with respect to specific embodiments, many modifications, variations, alterations, substitutions, and equivalents will be apparent to those skilled in the art. The present disclosure is not to be limited in scope by the specific embodiment described herein. Indeed, various modifications of the embodiments herein, in addition to those described herein, will be apparent to those of skill in the art from the foregoing description and accompanying drawings. Accordingly, the embodiments herein are to be considered as limited only by the spirit and scope of the disclosure (and claims), including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity may be repeated, any activity may be performed by multiple entities, and/or any element may be duplicated. Further, any activity or element may be excluded, the sequence of activities may vary, and/or the interrelationship of elements may vary. Unless clearly specified to the contrary, there is no requirement for any particular described or illustrated activity or element, any particular sequence or such activities, any particular size, speed, material, dimension or frequency, or any particular interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Where applicable, citations herein, whether by numerical indication or by other means, refer to one or more of the documents listed in the section entitled "References."

REFERENCES

The devices, systems, apparatuses, modules, compositions, computer program products, non-transitory computer readable medium, models, algorithms, and methods of various embodiments disclosed herein may utilize aspects (devices, systems, apparatuses, modules, compositions, computer program products, non-transitory computer readable medium, models, algorithms, and methods) disclosed in the following references, applications, publications and patents and which are hereby incorporated by reference herein in their entirety, and which are not admitted to be prior art with respect to the present embodiments by inclusion in this section:

A. International Patent Application Serial No. PCT/US2020/041528, entitled "SYSTEM AND METHOD FOR ONLINE DOMAIN ADAPTATION OF MODELS FOR HYPOGLYCEMIA PREDICTION IN TYPE 1 DIABETES", filed Jul. 10, 2020.

B. International Patent Application Serial No. PCT/US2020/032855, entitled "SYSTEM AND METHOD FOR ARTIFICIAL PANCREAS WITH MULTI-STAGE MODEL PREDICTIVE CONTROL", filed May 14, 2020.

C. U.S. Utility patent application Ser. No. 16/789,901, entitled "Unified Platform For Monitoring and Control of Blood Glucose Levels in Diabetic Patients", filed Feb. 13, 2020; Publication No. US-2020-0214629-A1, Jul. 9, 2020.

D. U.S. Utility patent application Ser. No. 14/128,922, entitled "Unified Platform For Monitoring and Control of Blood Glucose Levels in Diabetic Patients", filed Dec. 23, 2013; U.S. Pat. No. 10,610,154, issued Apr. 7, 2020.

E. International Patent Application Serial No. PCT/US2012/043910, entitled "Unified Platform For Monitoring and Control of Blood Glucose Levels in Diabetic Patients", filed Jun. 23, 2012; Publication No. WO 2012/178134, Dec. 27, 2012.

F. U.S. Utility patent application Ser. No. 16/588,881, entitled "Tracking the Probability for Imminent Hypoglycemia in Diabetes from Self-Monitoring Blood Glucose (SMBG) Data", filed Sep. 30, 2019; Publication No. US-2020-0066410-A1, Feb. 27, 2020.

G. U.S. Utility patent application Ser. No. 13/394,091, entitled "Tracking the Probability for Imminent Hypoglycemia in Diabetes from Self-Monitoring Blood Glucose (SMBG) Data", filed Mar. 2, 2012; U.S. Pat. No. 10,431,342, issued Oct. 1, 2019.

H. International Patent Application Serial No. PCT/US2010/047711, entitled "Tracking the Probability for Imminent Hypoglycemia in Diabetes from Self-Monitoring Blood Glucose (SMBG) Data", filed Sep. 2, 2010; Publication No. WO 2011/028925, Mar. 10, 2011.

I. U.S. Utility patent application Ser. No. 16/583,456, entitled "SYSTEM, METHOD, AND COMPUTER READABLE MEDIUM FOR DYNAMIC INSULIN SENSITIVITY IN DIABETIC PUMP USERS", filed Sep. 26, 2019; Publication No. US-2020-0023126-A1, Jan. 23, 2020.

J. International Patent Application Serial No. PCT/US2016/050109, entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. WO 2017/040927, Mar. 9, 2017.

K. U.S. Utility patent application Ser. No. 15/255,828, entitled "SYSTEM, METHOD, AND COMPUTER READABLE MEDIUM FOR DYNAMIC INSULIN

40

SENSITIVITY IN DIABETIC PUMP USERS", filed Sep. 2, 2016; U.S. Pat. No. 10,463,789, issued Nov. 5, 2019.

L. U.S. Utility patent application Ser. No. 16/577,398, entitled "Method, System and Computer Readable Medium for Predictive Hypoglycemia Detection for Mild to Moderate Exercise", filed Sep. 20, 2019; Publication No. US-2020-0015757-A1, Jan. 16, 2020.

M. U.S. Utility patent application Ser. No. 15/252,365, entitled "Method, System and Computer Readable Medium for Predictive Hypoglycemia Detection for Mild to Moderate Exercise", filed Aug. 31, 2016; U.S. Pat. No. 10,456,086, issued Oct. 29, 2019.

N. U.S. Utility patent application Ser. No. 16/546,335, entitled "System Coordinator and Modular Architecture for Open-Loop and Closed-Loop Control of Diabetes", filed Aug. 21, 2019; Publication No. US-2019-0374137-A1, Dec. 12, 2019.

O. U.S. Utility patent application Ser. No. 13/322,943, entitled "System Coordinator and Modular Architecture for Open-Loop and Closed-Loop Control of Diabetes", filed Nov. 29, 2011; U.S. Pat. No. 10,420,489, issued Sep. 24, 2019.

P. International Patent Application Serial No. PCT/US2010/036629, entitled "System Coordinator and Modular Architecture for Open-Loop and Closed-Loop Control of Diabetes", filed May 28, 2010; Publication No. WO 2010/138848, Dec. 2, 2010.

Q. U.S. Utility patent application Ser. No. 16/483,487, entitled "Method, System, and Computer Readable Medium for Controlling Insulin Delivery Using Retrospective Virtual Basal Rates", filed Aug. 5, 2019; Publication No. US-2020-0016336-A1, Jan. 16, 2020.

R. International Patent Application Serial No. PCT/US2018/016837, entitled "Method, System, and Computer Readable Medium for Controlling Insulin Delivery Using Retrospective Virtual Basal Rates", filed Feb. 5, 2018; Publication No. WO 2018/144992, Aug. 9, 2018.

S. U.S. Utility patent application Ser. No. 16/451,766, entitled "TRACKING CHANGES IN AVERAGE GLYCEMIA IN DIABETICS", filed Jun. 25, 2019; Publication No. US-2019-0318801-A1, Oct. 17, 2019.

T. U.S. Utility patent application Ser. No. 14/769,638, entitled "METHOD AND SYSTEM FOR MODEL-BASED TRACKING OF CHANGES IN AVERAGE GLYCEMIA IN DIABETES", filed Aug. 21, 2015; U.S. Pat. No. 10,332,615, issued Jun. 25, 2019.

U. International Patent Application Serial No. PCT/US2014/017754, entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.

V. U.S. Utility patent application Ser. No. 16/274,874, entitled "SYSTEM AND METHOD FOR PHYSICAL ACTIVITY INFORMED DRUG DOSING", filed Feb. 13, 2019; Publication No. US 2019/0252055 A1, Aug. 15, 2019.

W. U.S. Utility patent application Ser. No. 16/205,398, entitled "LQG Artificial Pancreas Control System and Related Method", filed Nov. 30, 2018; Publication No. US-2019-0099555-A1, Apr. 4, 2019.

X. U.S. Utility patent application Ser. No. 12/665,420, entitled "LQG Artificial Pancreas Control System and Related Method", filed Dec. 18, 2009; U.S. Pat. No. 10,173,006, issued Jan. 8, 2019.

Y. International Patent Application Serial No. PCT/US2008/067723, entitled "LQG Artificial Pancreas Control System and Related Method", filed Jun. 20, 2008; Publication No. WO 2008/157780, Dec. 24, 2008.

Z. U.S. Utility patent application Ser. No. 16/126,879, entitled "Method, System and Computer Program Product for Evaluation of Insulin Sensitivity, Insulin/Carbohydrate Ratio, and Insulin Correction Factors in Diabetes from Self-Monitoring Data", filed Sep. 10, 2018; Publication No. US-2019-0019571-A1, Jan. 17, 2019.

AA. U.S. Utility patent application Ser. No. 12/665,149, entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010.

BB. International Patent Application Serial No. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.

CC. U.S. Utility patent application Ser. No. 16/073,920, entitled "METHOD, SYSTEM, AND COMPUTER READABLE MEDIUM FOR VIRTUALIZATION OF A CONTINUOUS GLUCOSE MONITORING TRACE", filed Jul. 30, 2018; Publication No. US-2019-0043620-A1, Feb. 7, 2019.

DD. International Patent Application Serial No. PCT/US2017/015616, entitled "METHOD, SYSTEM, AND COMPUTER READABLE MEDIUM FOR VIRTUALIZATION OF A CONTINUOUS GLUCOSE MONITORING TRACE", filed Jan. 30, 2017; Publication No. WO 2017/132663, Aug. 3, 2017.

EE. U.S. Utility patent application Ser. No. 15/958,257, entitled "System, Method and Computer Readable Medium for Dynamical Tracking of the Risk for Hypoglycemia in Type 1 and Type 2 Diabetes", filed Apr. 20, 2018; Publication No. US-2018-0366223-A1, December 2018.

FF. International Patent Application Serial No. PCT/US2016/058234, entitled "System, Method and Computer Readable Medium for Dynamical Tracking of the Risk for Hypoglycemia in Type 1 and Type 2 Diabetes", filed Oct. 21, 2016; Publication No. WO 2017/070553, Apr. 27, 2017.

GG. U.S. Utility patent application Ser. No. 15/866,384, entitled "Method, System and Computer Program Product for Real-Time Detection of Sensitivity Decline in Analyte Sensors", filed Jan. 9, 2018; Publication No. US-2018-0323882-A1, Nov. 8, 2018.

HH. U.S. Utility patent application Ser. No. 14/266,612, entitled "Method, System and Computer Program Product for Real-Time Detection of Sensitivity Decline in Analyte Sensors", filed Apr. 30, 2014; U.S. Pat. No. 9,882,660, issued Jan. 30, 2018.

II. U.S. Utility patent application Ser. No. 13/418,305, entitled "Method, System and Computer Program Product for Real-Time Detection of Sensitivity Decline in Analyte Sensors", filed Mar. 12, 2012; U.S. Pat. No. 8,718,958, issued May 6, 2014.

JJ. International Patent Application Serial No. PCT/US2007/082744, entitled "Method, System and Computer Program Product for Real-Time Detection of Sensitivity Decline in Analyte Sensors", filed Oct. 26, 2007; Publication No. WO/2008/052199, May 2, 2008.

KK. U.S. Utility patent application Ser. No. 11/925,689, entitled "Method, System and Computer Program Product for Real-Time Detection of Sensitivity Decline in Analyte Sensors", filed Oct. 26, 2007; U.S. Pat. No. 8,135,548, issued Mar. 13, 2012.

LL. U.S. Utility patent application Ser. No. 15/580,935, entitled "INSULIN MONITORING AND DELIVERY SYSTEM AND METHOD FOR CGM BASED FAULT DETECTION AND MITIGATION VIA METABOLIC STATE TRACKING", filed Dec. 8, 2017; Publication No. US-2019-0254595-A1, Aug. 22, 2019.

MM. International Patent Application Serial No. PCT/US2016/036729, entitled "INSULIN MONITORING AND DELIVERY SYSTEM AND METHOD FOR CGM BASED FAULT DETECTION AND MITIGATION VIA METABOLIC STATE TRACKING", filed Jun. 9, 2016; Publication No. WO 2016/201120, Dec. 15, 2016.

NN. U.S. Utility patent application Ser. No. 15/580,915, entitled "System and Method for Tracking Changes in Average Glycemia in Diabetics", filed Dec. 8, 2017; Publication No. US-2018-0313815-A1, Nov. 1, 2018.

OO. International Patent Application Serial No. PCT/US2016/036481, entitled "System and Method for Tracking Changes in Average Glycemia in Diabetics", filed Jun. 8, 2016; Publication No. WO2016200970, Dec. 15, 2016.

PP. U.S. Utility patent application Ser. No. 15/669,111, entitled "METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY", filed Aug. 4, 2017; Publication No. US-2017-0337348-A1, Nov. 23, 2017.

QQ. U.S. Utility patent application Ser. No. 14/015,831, entitled "CGM-Based Prevention of Hypoglycemia Via Hypoglycemia Risk Assessment and Smooth Reduction of Insulin Delivery", filed Aug. 30, 2013; U.S. Pat. No. 9,750,438, issued Sep. 5, 2017.

RR. U.S. Utility patent application Ser. No. 13/203,469, entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

SS. International Patent Application Serial No. PCT/US2010/025405, entitled "CGM-BASED PREVENTION OF HYPOGLYCEMIA VIA HYPOGLYCEMIA RISK ASSESSMENT AND SMOOTH REDUCTION INSULIN DELIVERY", filed Feb. 25, 2010; Publication No. WO 2010/099313 A1, Sep. 2, 2010.

TT. U.S. Utility patent application Ser. No. 14/902,731, entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; U.S. Pat. No. 10,169,544, issued Jan. 1, 2019.

UU. International Patent Application Serial No. PCT/US2014/045393, entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO2015003124, Jan. 8, 2015.

VV. U.S. Utility patent application Ser. No. 14/419,375, entitled "COMPUTER SIMULATION FOR TESTING AND MONITORING OF TREATMENT STRATEGIES FOR STRESS HYPERGLYCEMIA", filed Feb. 3, 2015; U.S. Pat. No. 10,438,700, issued Oct. 8, 2019.

WW. International Patent Application Serial No. PCT/US2013/053664, entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.

XX. U.S. Utility patent application Ser. No. 14/128,811, entitled "Methods and Apparatus for Modular Power Management and Protection of Critical Services in Ambulatory Medical Devices", filed Dec. 23, 2013; U.S. Pat. No. 9,430,022, issued Aug. 30, 2016.

YY. International Patent Application Serial No. PCT/US2012/043883, entitled "Methods and Apparatus for Modular Power Management and Protection of Critical Services in Ambulatory Medical Devices", filed Jun. 22, 2012; Publication No. WO 2012/178113, Dec. 27, 2012.

ZZ. U.S. Utility patent application Ser. No. 13/637,359, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016.

AAA. International Patent Application Serial No. PCT/US2011/029793, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

BBB. U.S. Utility patent application Ser. No. 13/634,040, entitled "Method and System for the Safety, Analysis, and Supervision of Insulin Pump Action and Other Modes of Insulin Delivery in Diabetes", filed Sep. 11, 2012; Publication No. 2013/0116649, May 9, 2013.

CCC. International Patent Application Serial No. PCT/US2011/028163, entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.

DDD. U.S. Utility patent application Ser. No. 13/131,467, entitled "Method, System, and Computer Program Product for Tracking of Blood Glucose Variability in Diabetes", filed May 26, 2011; U.S. Pat. No. 9,317,657, issued Apr. 19, 2016.

EEE. International Patent Application Serial No. PCT/US2009/065725, entitled "Method, System, and Computer Program Product for Tracking of Blood Glucose Variability in Diabetes", filed Nov. 24, 2009; Publication No. WO 2010/062898, Jun. 3, 2010.

FFF. U.S. Utility patent application Ser. No. 12/674,348, entitled "Method, Computer Program Product and System for Individual Assessment of Alcohol Sensitivity", filed Feb. 19, 2010; Publication No. 2011/0264374, Oct. 27, 2011.

GGG. International Patent Application Serial No. PCT/US2008/073738, entitled "Method, Computer Program Product and System for Individual Assessment of Alcohol Sensitivity", filed Aug. 20, 2008; Publication No. WO 2009/026381, Feb. 26, 2009.

HHH. U.S. Utility patent application Ser. No. 12/664,444, entitled "Method, System and Computer Simulation Environment for Testing of Monitoring and Control Strategies in Diabetes", filed Dec. 14, 2009; U.S. Pat. No. 10,546,659, issued Jan. 28, 2020.

III. International Patent Application Serial No. PCT/US2008/067725, entitled "Method, System and Computer Simulation Environment for Testing of Monitoring and Control Strategies in Diabetes", filed Jun. 20, 2008; Publication No. WO 2008/157781, Dec. 24, 2008.

JJJ. U.S. Utility patent application Ser. No. 12/516,044, entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013. International Patent Application Serial No. PCT/US2007/085588, entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.

[1] M. Pallayova, S. Taheri, Targeting diabetes distress: the missing piece of the successful type 1 diabetes management puzzle. Diabetes Spectrum 27 (2) (2014) 143-149.

[2] M. Sussman, J. Benner, M. J. Haller. M. Rewers, R. Griffiths, Estimated lifetime economic burden of type 1 diabetes. Diabetes Technology & Therapeutics 22 (2) (2020) 121-130.

[3] American Diabetes Association, Approaches to glycemic treatment, sec. 7., Diabetes care 39 (Supplement 1) (2016) S52-S59.

[4] Diabetes Control and Complications Trial Research Group, The effect of intensive treatment of diabetes on the development and progression of long-term complications in insulin-dependent diabetes mellitus. New England journal of medicine 329 (14) (1993) 977-986.

[5] J. M. Lachin, S. Genuth, D. M. Nathan, B. Zinman, B. N. Rutledge, et al., Effect of glycemic exposure on the risk of microvascular complications in the diabetes control and complications trial—revisited, Diabetes 57 (4) (2008) 995-1001.

[6] P. E. Cryer, Glycemic goals in diabetes: trade-off between glycemic control and iatrogenic hypoglycemia, Diabetes 63 (7) (2014) 2188-2195.

[7] C. D. Stehouwer, Microvascular dysfunction and hyperglycemia: a vicious cycle with widespread consequences. Diabetes 67 (9) (2018) 1729-1741.

[8] B. Kovatchev. W. V. Tamborlane, W. T. Cefalu, C. Cobelli. The artificial pancreas in 2016: a digital treatment ecosystem for diabetes, Diabetes Care 39 (7) (2016) 1123-1126.

[9] B. Kovatchev, S. M. Anderson. D. Raghinaru, Y. C. Kudva, L. M. Laffel, C. Levy. J. E. Pinsker, R. P. Wadwa, B. Buckingham, F. J. Doyle, et. al., Randomised controlled trial of mobile closed-loop control, Diabetes care 43 (3) (2020) 607-615.

[10] F. J. Doyle, L. M. Huyett, J. H. Lee, H. C. Zisser, E. Dassau, Closed-loop artificial pancreas systems: engineering the algorithms, Diabetes care 37 (5) (2014) 1191-1197.

[11] R. Hovorka, J. M. Allen, D. Elleri, L. J. Chassin, J. Harris, D. Xing, C. Kollman, T. Hovorka, A. M. P.

Larsen, M. Nodule, et al. Manual closed-loop insulin delivery in children and adolescents with type 1 diabetes: a phase 2 randomised crossover trial, The Lancet 375 (9716) (2010) 743-751.

[12] R. M. Bergenstal, S. Garg, S. A. Weinzimer, B. A. Buckingham, B. W. Bode, W. V. Tamborlane, F. R. Kaufman, Safety of a hybrid closed-loop insulin delivery system in patients with type 1 diabetes. Jama 316 (13) (2016) 1407-1408.

[13] S. A. Brown, B. P. Kovatchev, D. Raghinaru, J. W. Lum, B. A. Buckingham, Y. C. Kudva, L. M. Laffel, C. J. Levy, J. E. Pinsker, R. P. Wadwa, et al., Six-month randomized, multicenter trial of closed-loop control in type 1 diabetes, New England Journal of Medicine 381 (18) (2019) 1707-1717.

[14] M. D. Breton, L. G. Kanaspka, R. W. Beck. L. Ekhlaspour. G. P. Forlenza, E. Cengiz, M. Schoelwer, K. J. Ruedy, E. Jost, L. Carria, et al., A randomized trial of closed-loop control in children with type 1 diabetes, New England Journal of Medicine 383 (9) (2020) 836-845.

[15] R. Sanchez. D. R. Cherñavvsky (Eda.), Artificial Pancreas: Current Situation and Future Directions, Academic Press, 20319.

[16] S. J. Russell, M. A. Hillard, C. Balliro, K. L. Magyar. R. Selagamsetty, M. Sinba. K. Grennan, D. Mondesir, L. Ekhlaspour, H. Zheng, et al., Day and night glycaemic control with a bionic pancreas versus conventional insulin pump therapy in preadolescent children with type 1 diabetes: at randomised crossover trial, The lancet Diabetes & endocrinology 4 (3) (2016) 233-243.

[17] E. Dassau, J. E. Pinsker. Y. C. Kudva, S. A. Brown, R. Gondhalekar, C. Dalla Man, S. Patek, M. Schiavon, V. Dadlani, I. Dasanayake, et al., Twelve-week 24/7 ambulatory artificial pancreas with weekly adaptation of insulin delivery settings: effect on hemoglobin a1c and hypoglycemia, Diabetes Care 40 (12) (2017) 1719-1726.

[18] A. Brazeau, H. Mircescu, K. Desjardins, C. Leroux, I. Strychar, J. Ekoé, R. Rabasa-Lhoret, Carbohydrate counting accuracy and blood glucose variability in adults with type 1 diabetes, Diabetes research and clinical practice 99 (1) (2013) 19-23.

[19] J. B. Lee, E. Dssau, R. Gondhalekar, D. E. Seborg, J. E. Pinker. F. J. Doyle III, Enhanced model predictive control (empc) strategy for automated glucose control, Industrial & engineering chemistry research 55 (46) (2016) 11857-11868.

[20] D. Shi. E. Dassau. F. J. Doyle, Adaptive zone model predictive control of artificial pancreas bused on glucose- and velocity-dependent control penalties, IEEE Transactions on Biomedical Engineering 66 (4) (2018) 1045-1054.

[21] R. Gondhalekar, E. Dassau, F. J. Doyle III. Velocity-weighting & velocity-penalty rope an artificial pancreas: Improved safety & performance, Automatica 91 (2018) 105-117.

[22] P. Colmegna, F. Garelli. H. De Batista, R. Sánchez-Peña, Automatic regulatory control in type 1 diabetes without carbohydrate counting, Control Engineering Practice 74 (2018) 22-32.

[23] E. Fushimi, P. Colmegna, H. De Battista, F. Garelli. R. Sánchez-Peña, Artificial pancreas: Evaluating the arg algorithm without meal announcement, Journal of Diabetes Science and Technology 13 (6) (2019) 1035-1043.

[24] A. Chakrabarty, E. Healey, D Shi, S. Zavitsanou, F. J. Doyle, E. Dassau, Embedded model predictive control for a wearable artificial pancreas. IEEE Transactions on Control Systems Technology (2019).

[25] R. Mausmeth, I. B. Hirsch. J. Bollyky, R. Kircher. D. Matheson, S. Sanda, C. Greenbaum, Use of a "fuzzy logic" contoller in a closed-loop artificial pancreas, Diabetes technology & therapeutics 15 (8) (2013) 628-633.

[26] E. Dassau. H. Zisser, R. A. Harvey. M. W. Percival. B. Grosman. W. Bevier, E. Atlas, S. Miller, R. Nimri, L. Jovamovič, et al., Clinical evolution of a personalized artificial pancreas, Diabetes care 36 (4) (2113) 801-809.

[27] H. Blauw. A. Vain Bon, R. Koops, J DeVries, Performance and safety of an integrated bihormonal artificial pancreas for fully automated glucose control at home, Diabetes, Obesity and Metabolism 18 (7) (2016) 671-677.

[28] K. Turksoy, I. Hajizadeh, S. Samadi, J. Feng, M. Sevil, M. Park, L. Quinn, E. Littlejohn, A. Cinar, Real-time insulin bolusing for unannounced meals with artificial pancreas, Control Engineering Practice 59 (2017) 159-164.

[29] F. M. Cameron, T. T. Ly, B. A. Buckingham, D. M. Maahs, G. P. Forlenza, C. J. Levy, D. Lam, P. Clinton, L. H. Messer, E. Westfall, et al., Closed-loop control without meal announcement in type 1 diabetes. Diabetes technology & therapeutics 19 (9) (2017) 527-532.

[30] G. P. Forlenza, F. M. Cameron, T. T. Ly, D. Lam, D. P. Howsmon, N. Baysal, G. Kulina, L. Messer, P. Clinton, C. Levister, et al., Fully closed-loop multiple model probabilistic predictive controller artificial pancreas performance in adolescents and adults in a supervised hotel setting, Diabetes technology & therapeutics 20 (5) (2018) 335-343.

[31] J. Garcia-Tirado, P. Colmegna, J. P. Corbett, B. Ozaslam, M. D. Breton, In silico analysis of an exercise-safe artificial pancreas with multistage model predictive control and insulin safety system, Journal of diabetes science and technology 13 (6) (2019) 1054-1064.

[32] S. A. Brown, B. P. Kovatchev, M. D. Breton, S. M. Anderson, P. Keith-Hynes, S. D. Patek, B. Jiang, N. Ben Brahim, P. Vereshchetin, D. Bruttomesso, et al., Multimight "bedside" closed-loop control for patients with type 1 diabetes, Diabetes technology & therapeutics 17 (3) (2015) 203-209.

[33] R. Visentin, E. Campos-Náñez, M, Schiavon, D. Lv, M. Vettoretti, M. Breton, B. Kovatchev, C. Dalla Man, C. Cobelli, The UVA/Padovu type I diabetes simulator goes from single meal to single day. J Diabetes Sci Technol 17 (2) (2018) 273-281.

[34] J. Closed-Tirado, J. P. Corbett, D. Boiroux, J. B. Jorgensen, M. D. Breton, Closed-loop control with unannounced exercise for adults with type 1 diabetes using the ensemble model predictive control, Journal of Process Control 80 (2019) 202-210.

[35] C. Dalla Man, D. M. Raimondo, R. A. Rizza, C. Cobelli, Gim, simulation software of meal glucose—insulin model (2007).

[36] S. D. Patek, D. Lv, E. A. Ortiz., C. Hughes-Karvetski, S. Kulkarni, Q. Zhang, M. D. Breton. Empirical representation of blood glucose variability in a compartmental model, in: Prediction Methods for Blood Glucose Concentration. Sprinter, 2016, pp. 133-157.

[37] R. Sanz., P. García. J.-L. Díez, J. Bondia. Artificial pancreas system with unannounced meals based on a disturbance observer and feed-forward compensation. IEEE Transactions on Control Systems Technology (2020).

[38] J. Garcia-Tirado, C. Zuluaga-Bedoya, M. D. Breton, Identifiability analysis of three control-oriented models for use in artificial pancreas systems, J Diabetes Sci Technol 12 (5) (2018) 937-952. doi: 10.1177/1982295818788873.

[39] E. F. Camacho, C. B. Alba, Model predictive control, Springer Science & Business Media, 2013.

[40] J. B. Rawlings, D. Q. Mayne, M. Diehl, Model predictive control: theory, computation, and design, Vol. 2, Nob Hill Publishing Madison, WI, 2017.

[41] K. L. Swan, J. D. Dziura. G. M. Steil, G. R. Voskanyan, K. A. Sikes, A. T. Steffen, M. L. Martin, W. V. Tamborlane, S. A. Weinzimer, Effect of age of infusion site and type of rapid-acting analog on pharmacodynamic parameters of insulin boluses in youth with type 1 diabetes receiving insulin pump therapy, Diabetes Care 32 (2) (2009) 244-244.

[42] D. Boimux. A. K. Duun-Henriksen, S. Schmidt, K. Nørgaard, S. Madsbad, N. K. Poulsen, H. Madsen, J. B. Jørgensen. Overnight glucose control in people with type 1 diabetes, Biomedical Signal Processing and Control 39 (2018) 503-512. doi: 10.1016/j.bspr.2017.08.005.

[43] J. Garcia-Tirado, P. Colmegna, J. Corbett, B Ozaslan. M. D. Breton, Ensemble model predictive control strategies can reduce exercise hypoglycemia in type 1 diabetes: In silico studies, in: 2019 American Control Conference (ACC), 2019. pp. 4752-4758. doi: 10.23912/ACC.2019.8014728.

[44] T. Danne, R. Nimri, T. Battlelino, R. M. Bergenstal. K. L. Close, J. H. DeVries, S. Garg, L. Heinemann, I. Hirsch, S. A. Amiel, et al., International consensus on use of continuous glucose monitoring, Diabetes care 40 (92) (2017) 1631-1640.

[45] J. Garcia-Tirado, S. A. Brown, N. Laichuthai, P. Colmegna, C. L. Koravi, B. Ozaslan, J. P. Corbett, C. L. Barnett, M. Pajewski, M. C. Oliveri, et al., Anticipation of historical exercise patterns by a novel artificial pancreas system reduces hypoglycemia during and after moderate-intensity physical activity in people with type 1 diabetes. Diabetes Technology & Therapeutics 23 (4) (2021).

[46] C. Ellingsen, E. Dassau, H Zisser, B Grosman, M. W. Percival, L. Jovanovič, F. J. Doyle III, Safety constraints in an artificial pancreatic β cell: an implementation of model predictive control with insulin on board. Journal of diabetes science and technology 3 (3) (2009) 536-544.

[47] P. Colmegoa, K. Wang, J. Garcia-Tirado, M. D. Breton, Mapping data to virtual patients in type 1 diabetes, Control Engineering Practice 103 (2020) 104605.

[48] T. T. Ly, M. D. Breton, P. Keith-Hynes, D. De Salvo, P. Clinton, K. Benassi, B. Mize, D. Chernavvsky, J. Place, D. M. Wilson, et al., Overnight glucose control with an automated, unified safety system in children and adolescents with type 1 diabetes at diabetes camp. Diabetes care 37 (8) (2014) 2310-2316.

[49] M. Breton, J. Garcia-Tirado, H. Myers, C. Barnett, C. Koravi, N. Laichuthai, S. Brown, Clinical trial results of an artificial pancreas (ap) system that anticipates

[50] J. Garcia-Tirado, S. A. Brown, N. Laichutai, H. E. Myers, M. D. Breton, Anticipating regular physical activity with a new artificial pancreas system: A pilot study, Diabetes 69 (Supplement 1) (2020), doi: 18.2337/db20-030-P.

[51] B. P. Kovatchev, Metrics for glycaemic control—from bba1c to continuous glucose monitoring, Nature Reviews Endocrinology 13 (7) (2017) 425-436.

[52] Burdick J, Chase H P, Slover R H, et al. Mixed insight meal boluses and elevated hemoglobin A(1c) levels in children receiving insulin pump therapy. *Pediatrics* 2004; 113(3):E221-E224.

[53] Olinder A L, Kernell A, & Smile B, Missed bolus doses: devastating for metabolic control to CSII-treated adolescents with type 1 diabetes. *Pediatric Diabetes.* 2009; 10(2):142-148.

[54] Foster N C, Beck R W, Miller K M, et al. State of Type 1 Diabetes Management and Outcomes from the T1D Exchange in 2016-2018. *Diabetes Technol Ther.* 2019; 21(2):66-72.

What is claimed is:

1. In an artificial pancreas (AP), a processor-implemented method of regulating glycemia for a subject having Type 1 diabetes (T1D), comprising:
predicting glycemia values for the subject based on continuous glucose monitor (CGM) measurements of the subject;
determining a schedule of basal insulin dosing according to the predicted values;
modifying the schedule according to detection, from the CGM measurements, of a predetermined value of one or more of the CGM measurements and an increasing rate of change of the CGM measurements, and defining a modified schedule according to the modification;
delivering the schedule or the modified schedule to the subject;
calculating a probability that a glycemic disturbance, which was not announced to the AP, occurred within a predetermined period; and
supplementing the delivery of the schedule or the modified schedule with an automatic delivery of a first bolus of insulin in response to the calculated probability.

2. The method of claim 1, wherein:
the schedule and the modified schedule each minimize a cost function comprising terms to (a) correct the subject's glycemia level(s) to a predetermined target level, (b) penalize predicted glycemia values trending toward hypoglycemia, and (c) weight a difference amount between predictions of two consecutive basal insulin doses.

3. The method of claim 2, wherein:
the glycemic disturbance comprises a meal comprising a carbohydrate content, and the calculated probability is based on the CGM measurements for the predetermined period.

4. The method of claim 3, wherein:
the calculated probability is calculated at each of successive intervals of the CGM measurements, each interval being included within the predetermined period.

5. The method of claim 4, wherein:
the first bolus comprises a predetermined percentage of total daily insulin (TDI) of the subject.

6. The method of claim 5, wherein:
the predetermined percentage increases as the calculated probability increases.
7. The method of claim 6, wherein:
with respect to a series of first boluses, a subsequent one thereof is decreased by an amount of insulin on board (IOB) equal to each of antecedent first boluses.
8. The method of claim 7, further comprising:
based on the predicted glycemia values indicating hypoglycemia, automatically decreasing the basal insulin dosing to a fraction of an average therefor.
9. The method of claim 8, further comprising:
automatically supplementing the delivery of the schedule or the modified schedule with a delivery of a second bolus of insulin (a) in response to the current glycemia value and the predicted glycemia values indicating hyperglycemia and (b) after the delivery of the first bolus.
10. The method of claim 9, wherein:
the delivery of the second bolus is blocked within two (2) hours after delivery of the first bolus.
11. The method of claim 10, wherein:
a frequency of the delivery of the second bolus is limited to once per hour.
12. The method of claim 11, further comprising:
suspending the automatic delivery of the first bolus in response to announcement of the meal to the AP, and supplementing the delivery of the schedule or the modified schedule with a delivery of a third bolus calculated as one-half of a bolus based on the subject's insulin-carbohydrate ratio (CR) and a correction factor (CF).
13. A control system of an artificial pancreas (AP) defining a controller therefor and comprising:
a processor;
a processor-readable memory comprising processor-executable instructions for:
predicting glycemia values for a subject based on continuous glucose monitor (CGM) measurements of the subject;
determining a schedule of basal insulin dosing according to the predicted values;
modifying the schedule according to detection, from the CGM measurements, of a predetermined value of one or more of the CGM measurements and an increasing rate of change of the CGM measurements, and defining a modified schedule according to the modification;
initiating delivery of the schedule or the modified schedule to the subject;
calculating a probability that a glycemic disturbance, which was not announced to the controller, occurred within a predetermined period; and
supplementing the delivery of the schedule or the modified schedule with an automatic delivery of a first bolus of insulin in response to the calculated probability; and
causing the delivery of the schedule or the modified schedule to be supplemented with an automatic delivery of a first bolus of insulin in response to the calculated probability.

14. The system of claim 13, wherein:
the schedule and the modified schedule each minimize a cost function comprising terms to (a) correct the subject's glycemia level(s) to a predetermined target level, (b) penalize predicted glycemia values trending toward hypoglycemia, and (c) weight a difference amount between predictions of two consecutive basal insulin doses.
15. The system of claim 14, wherein:
the glycemic disturbance comprises a meal comprising a carbohydrate content, and the calculated probability is based on the CGM measurements for the predetermined period.
16. The system of claim 15, wherein:
the calculated probability is calculated at each of successive intervals of the CGM measurements, each interval being included within the predetermined period.
17. A non-transitory computer-readable medium having stored thereon computer-executable instructions for regulating, in an artificial pancreas (AP), glycemia values for a subject having Type 1 diabetes (T1D), said instructions causing a computer to:
predict glycemia values for the subject based on continuous glucose monitor (CGM) measurements of the subject;
determine a schedule of basal insulin dosing according to the predicted values;
modify the schedule according to detection, from the CGM measurements, of a predetermined value of one or more of the CGM measurements and an increasing rate of change of the CGM measurements, and defining a modified schedule according to the modification;
initiate delivery of the schedule or the modified schedule to the subject; and
calculate a probability that a glycemic disturbance, which was not announced to the AP, occurred within a predetermined period; and
cause the delivery of the schedule or the modified schedule to be supplemented with an automatic delivery of a first bolus of insulin in response to the calculated probability.
18. The medium of claim 17, wherein:
the schedule and the modified schedule each minimize a cost function comprising terms to (a) correct the subject's glycemia level(s) to a predetermined target level, (b) penalize predicted glycemia values trending toward hypoglycemia, and (c) weight a difference amount between predictions of two consecutive basal insulin doses.
19. The medium of claim 18, wherein:
the glycemic disturbance comprises a meal comprising a carbohydrate content, and the calculated probability is based on the CGM measurements for the predetermined period.
20. The medium of claim 19, wherein:
the calculated probability is calculated at each of successive intervals of the CGM measurements, each interval being included within the predetermined period.

* * * * *